US007741052B2

(12) United States Patent
Ladenson et al.

(10) Patent No.: US 7,741,052 B2
(45) Date of Patent: Jun. 22, 2010

(54) METHOD OF ASSESSING THE RISK OF ATHEROSCLEROSIS

(75) Inventors: Jack H. Ladenson, St. Louis, MO (US); Pampee P. Young, Brentwood, TN (US); Vijay Modur, Norristown, PA (US)

(73) Assignee: Washington University in St. Louis, St. Louis, MO (US)

( * ) Notice: Subject to any disclaimer, the term of this patent is extended or adjusted under 35 U.S.C. 154(b) by 1061 days.

(21) Appl. No.: 11/120,318

(22) Filed: May 2, 2005

(65) Prior Publication Data

US 2005/0266497 A1 Dec. 1, 2005

Related U.S. Application Data

(60) Provisional application No. 60/567,420, filed on Apr. 30, 2004.

(51) Int. Cl.
*G01N 33/53* (2006.01)
*G01N 33/48* (2006.01)
(52) U.S. Cl. ..................................... 435/7.1; 435/40.52
(58) Field of Classification Search ....................... None
See application file for complete search history.

(56) References Cited

OTHER PUBLICATIONS

Steinert et al., "Transglutaminase crosslinking and structural studies of the human small proline rich 3 protein" (1999) Cell Death and Differentiation (1999) 6, 916-930.*
Cabral et al. "Structural Organization and Regulation of the Small Proline-rich Family of Cornified Envelope Precursors Suggest a Role in Adaptive Barrier Function" J Biol Chem. Jun. 1, 2001; 276(22):19231-7.*
Burtis, C.A. (Ed.), Tietz Textbook of Clinical Chemistry, 3rd Edition, (1999), W.B. Saunders Company, Philadelphia, PA, p. 477.*
Information Hyperlinked Over Proteins (iHOP), entry information for Sprr3 and SPRR3, retrieved from http://www.ihop-net.org/UniPub/iHOP/mgi/124857.html and from http://www.ihop-net.org/UniPub/iHOP/gs/92372.html, respectively, on Jun. 10, 2009 (2 pages total).*
"EST70772", retrieved from http://www.ncbi.nlm.nih.gov/entrez/viewerfcgi?db=protein&val=2013806 on Nov. 9, 2009 (2 pages).
"Homo sapiens small proline —rich protein 3 (SPRR3)", retrieved from http://www.ncbi.nlm.nih.gov/entrez/viewerfcgi?db=nucleotide&val=4885606 on Nov. 9, 2009 (4 pages).
"Chapter 2: Histochemistry— Introduction", retrieved from http://homepages.gac.edu/~cellab/chpts/chpt2/intro2.html. On Jan. 19, 2010 (6 pages).
Monoclonal Antibody Production, a Report of the Committee on Methods of Producing Monoclonal Antibodies Institute for Laboratory Animal Research National Research council, National Academy Press, Washington DC 1999.
"Clinical Laboratory Methods for Detection of Antigens & Antibodies", Basic and Clinical Immunology (Stites & Terr eds.,) 7th ed. 1991., Chapter 18, pp. 217-262.
"Enzyme-Linked Immunosorbent Assay (ELISA)", Chapter 8 in: Clark et al., Enzyme Immunoassay (Maggio, ed., 1980), pp. 167-179.

"Strategies for Cloning in Plasmic Vectors", Sambrook et al., 1989, Molecular Cloning, A Laboratory Manual, Cold Spring Harbor Press, N.Y., pp. 1.53-1.73.
Wolff et al., PNAS 86:9011-9014 (1989).
Rosenberg et al., Science 242:1575-1578 (1988).
Caplen et al., Nature Med., 1:39-46 (1995).
Zhu et al., Science, 261:209-211 (1993).
Stehbens WE: Structural and architectural changes during arterial development and the role of hemodynamics. Acta Anat 1996, 157:261-274.
Mills I, Sumpio BE: Vascular smooth muscle cells. Armonk, New York, Futura Publishing Company, Inc., 1997, pp. 187-226.
Fry DL: Arterial intimal-medial permeability and coevolving structural responses to defined shear-stress exposures. Am J Physiol Heart Circ Physiol 2002, 283:H2341-H2355.
Schwartz SM, Majesky MW, Murry CE: The intima: development and monoclonal responses to injury. Atherosclerosis 1995, 118:S125-S140.
Cleaver O, Melton DA: Endothelial signaling during development. Nature Med 2003, 9:661-668.
Carmeliet P: Angiogenesis in health and disease. Nature Med 2003, 9:653-660.
Curto EV, Lambert GW, Davis RL, Wilborn TW, Dooley TP: Biomarkers of human skin cells identified using dermarray DNA arrays and new bioinformatics methods. Biochem Biophys Res Comm 2002, 291:1052-1064.
Marenholz I, Zirra M, Fischer DF, Backendort C, Ziegler A, Mischke D: Identification of human epidermal differentiation complex (EDC)-encoded genes by subtractive hybridization of entire YACs to a gridded keratinocyte cDNA library. Genome Res 2001, 11:341-355.
Kalinin AE, Kajava AV, Steinert PM: Epithelial barrier function: assembly and structural features of the cornified cell envelope. BioEssays 2002, 24:789-800.
Gibbs S, Funeman R, Wiegant J, Geurts van Kessel A, Putte P, Backendorf C: Molecular characterization and evolution of the SPRR family of keratinocyte differentiation markers encoding small proline-rich proteins. Genomics 1993, 16:630-637.
Jamik M, Kartasove T, Steinert PM, Lichti U, Steven AC: Differential expression and cell envelope incorporation of small proline-rich protein 1 in different cornified epithelia. J Cell Science 1996, 109:1381-1391.
Nemes Z, Steinert PM: Bricks and mortar of the epidermal barrier. Exp Mol Med 1999, 31:5-19.

(Continued)

*Primary Examiner*—Mark L Shibuya
*Assistant Examiner*—Christine Foster
(74) *Attorney, Agent, or Firm*—Armstrong Teasdale LLP

(57) ABSTRACT

A method for aiding in the determination of whether a living or deceased human is afflicted with or will likely have atherosclerosis respectfully, the method comprising determining the level of SPRR3 protein in a intimae or body fluid sample by using molecular localization analysis technique comparing the determined level of SPRR3 protein in the biological sample obtained from said individual with a range of SPRR3 levels previously defined as characteristic for humans having atherosclerosis, concluding from the comparison that the person is likely suffering from atherosclerosis when a SPRR3 level is in the range previously defined as characteristic for the presence of atherosclerosis as an indication that the individual is suffering from or has suffered from atherosclerosis.

8 Claims, 9 Drawing Sheets

OTHER PUBLICATIONS

Bonilla IE, Tanabe K, Strittmatter SM: Small proline-rich repeat protein 1A is expressed by axotomized neurons and promotes axonal outgrowth. J Neuroscience 2002, 22:1303-1315.

Champliaud M, Baden HP, Koch M, Jin W, Burgeson RE, Viel A: Gene characterization of sciellin (SCEL) and protein localization in vertebrate epithelia displaying barrier properties. Genomics 2000, 70:264-268.

Baden HP, Kvedar JC: Epithelial cornified envelope precursors are in the hair follicle. J Invest Dermatol 1993, 101:72S-74S.

Kwei S, Stavrakis G, Takahas M, Taylor G, Folkman MJ, Gimbrone MA, Garcia-Cardena G: Early adaptive responses of the vascular wall during venous arterialization in mice. Am J Pathol 2004, 164:81-89.

Karashima T, Watt FM: Interaction of periplakin and envoplakin with intermediate filaments. J Cell Science 2002, 115:5027-5037.

Fuchs E, Weber K: Intermediate filaments: structure, dynamics, function, and disease. Annu Rev Biochem 1994, 63:345-382.

Waseem A, Alam Y, Dogan B, White KN, Leigh IM, Waseem NH: Isolation, sequence and expression of the gene encoding human keratin 13. Gene 1998, 215:269-279.

Johansson B, Eriksson A, Thornell L: Intermediate filament proteins in developing human arteries. Anat Embryol 1999, 199:225-231.

Marshall D, Hardman MJ, Nield KM, Byrne C: Differentially expressed late constituents of the epidermal cornified envelope. Proc Natl Acad Sci, USA 2001, 98:13031-13036.

North AJ, Bardsley WG, Hyam J, Bornslaeger EA, Cordingley HC, Trinnaman B, Hatzfeld M, Green KJ, Magee AI, Garrod DR: Molecular map of the desmosomal plaque. J Cell Science 1999, 4325-4336.

Vestweber D: Molecular mechanisms that control endothelial cell contacts. J Pathol 2000, 190:281-291.

Gallicano GI, Bauer C, Fuchs E: Rescuing desmoplatkin function in extra-embryonic ectoderm reveals the importance of this protein in embryonic heart, neuroepithelium, skin and vasculature. Development 2001, 128:929-941.

Schnittler HJ, Puschel B, Drenchkhahn D: Role of cadherins and plakoglobin in interendothelial adhesion under resting conditions and shear stress. Am J Physiol Heart Circ Physiol 1997, 273:H23296-H22405.

Troyanovsky RB, Chitaev NA, Troyanovsky SM: Cadherin binding sites of plakoglobin: localization, specificity and role in targeting to adhering junctions. J. Cell Science 1996, 109:3069-3078.

Hoffmann I, Mertens C, Brettel M, Nimmrich V, Schnolzer M, Herrmann H: Interaction of plakophilins with desmoplakin and intermediate filament proteins: an in vitro analysis. J Cell Science 2000, 113:2471-2483.

Magnaldo T, Darmon M: Galectin-7, a new marker of mammalian stratified epithelia. Trends Glycoscience Glycotechnology 1997, 9:95-102.

Timmons PM, Colnot C, Cail I, Poirier F, Magnaldo T: Expression of galectin-7 during epithelial development coincides with the onset of stratification. Int J Dev Diol 1999, 43:229-235.

Haroon Z, Wannenburg T, Gupta M, Greenberg CS, Wallin R, Sane DC: Localization of tissue transglutaminase in human carotid and coronary artery atherosclerosis: implications for plaque stability and progression. Lab Invest 2001, 81:83-93.

Gale NW, Baluk P, Pan L, Kwan M, Holash J, DeChiara TM, McDonald DM, Yancopoulos GD: Ephrin-B2 selectively marks arterial vessels and neovascularization sites in the adult, with expression in both endothelial and smooth muscle cells. Develop Biol 2001, 230:151-160.

Lawson ND, Vogel AM, Weinstein BM: Sonic hedgehog and vascular endothelial growth factor acts upstream of the notch pathway during arterial endothelial differentiation. Develop Cell 2002, 3:127-136.

Zhong TP, Childs S, Leu JP, Fishman MC: Gridlock signalling pathway fashions the first embryonic artery. Nature 2001, 414:216-220.

Lawson ND, Weinstein BM: Arteries and veins: making a difference with zebrafish. Nature Rev 2002, 3:674-682.

Garcia-Cardena G, Comander J, Anderson DJ, Blackman BR, Gimbrone MA: Biomechanical activation of vascular endothelium as a determinant of its functional phenotype. Proc Natl Acad Sci, USA 2001, 98:4478-4485.

Dekker RJ, van Soest S, Fontijn RD, Salamanca S, de Groot PG, VanBavel E, Pannekoek H, Horrevoets AJ: Prolonged fluid shear stress induces a distinct set of endothelial cell genes, most specifically lung Kruppel-like factor (KLF2). Blood 2002, 100:1689-1698.

Chen BP, Li Y, Zhao Y, Chen K, Li S, Lao J, Yuan S, Shyy JY, Chien S: DNA microarray analysis of gene expression in endothelial cells in response to 24-h shear stress. Physiol Genomics 2001, 7:55-63.

Wasserman SM, HMehraban F, Komuves LG, Yang R, Tomlinson JE, Zhang Y, Spriggs F, Topper JN: Gene expression profile of human endothelial cells exposed to sustained fluid shear stress. Physiol Genomics 2002, 12:13-23.

Salunke NV, Topoleski LDT, Humphrey JD, Mergner WJ: Compressive stress-relaxation of human atherosclerotic plaque. J Biomed Mater Res 2001, 55:236-241.

Kohler & Milstein, Eur. J Immunol. 6:511-519 (1976).

Huse et al., Science 246:1275-1281 (1989).

"Production of Antibodies" and "Production of Monoclonal Antibodies", Units 2.4 and 2.5 in: Colligan, Current Protocols in Immunology (1991), pp. 2.4.1-2.5.17.

Goding, Monoclonal Antibodies: Principles and Practice (2d ed. 1986), pp. 59-88.

Kohler & Milstein, Nature, 256:495-497 (1975).

Ward et al., Nature 341:544-546 (1989).

Hodgson et al., BioTechnology 13:222 (1995).

* cited by examiner

SEQUENCE LISTING

<160> NUMBER OF SEQ ID NOS: 2

<210> SEQ ID NO 1
<211> LENGTH: 169
<212> TYPE: PRT
<213> ORGANISM: Homo sapiens

<400> SEQUENCE: 1

```
Met Ser Ser Tyr Gln Gln Lys Gln Thr Phe Thr Pro Pro Pro Gln Leu
  1               5                  10                  15

Gln Gln Gln Gln Val Lys Gln Pro Ser Gln Pro Pro Gln Glu Ile
             20                  25                  30

Phe Val Pro Thr Thr Lys Glu Pro Cys His Ser Lys Val Pro Gln Pro
             35                  40                  45

Gly Asn Thr Lys Ile Pro Glu Pro Gly Cys Thr Lys Val Pro Glu Pro
         50                  55                  60

Gly Cys Thr Lys Val Pro Glu Pro Gly Cys Thr Lys Val Pro Glu Pro
 65                  70                  75                  80

Gly Cys Thr Lys Val Pro Glu Pro Gly Cys Thr Lys Val Pro Glu Pro
                 85                  90                  95

Gly Cys Thr Lys Val Pro Glu Pro Gly Tyr Thr Lys Val Pro Glu Pro
                100                 105                 110

Gly Ser Ile Lys Val Pro Asp Gln Gly Phe Ile Lys Phe Pro Glu Pro
            115                 120                 125

Gly Ala Ile Lys Val Pro Glu Gln Gly Tyr Thr Lys Val Pro Val Pro
        130                 135                 140

Gly Tyr Thr Lys Leu Pro Glu Pro Cys Pro Ser Thr Val Thr Pro Gly
145                 150                 155                 160

Pro Ala Gln Gln Lys Thr Lys Gln Lys
                165
```

<210> SEQ ID NO 2
<211> LENGTH: 984
<212> TYPE: DNA
<213> ORGANISM: Homo sapiens

<400> SEQUENCE: 2

```
accagatccc agaggctgaa cacctcgacc ttctctgcac agcagatgat ccctgagcag      60
ctgaagacca gaaaagccac taagactttc tgcttaattc aggagcttag aggattcttc     120
aaagagtgtg tccacgatcc tttgaagcat gagttcttac cagcagaagc agacctttac     180
cccaccacct cagcttcaac agcagcaggt gaaacaaccc agccagcctc cacctcagga     240
aatatttgtt cccacaacca aggagccatg ccactcaaag gttccacaac ctggaaacac     300
aaagattcca gagccaggct gtaccaaggt ccctgagcca ggctgtacca aggtccctga     360
gccaggctgt accaaggtcc ctgagccagg ttgtaccaag gtccctgagc aggctgtac     420 caaggtccct gagccaggtt gtaccaaggt ccctgagcca ggctacacca aggtccctga     480
accaggcagc atcaaggtcc ctgaccaagg cttcatcaag tttcctgagc caggtgccat     540
caaagttcct gagcaaggat acaccaaagt tcctgtgcca ggctacacaa agctaccaga     600
```

-continued

```
gccatgtcct tcaacggtca ctccaggccc agctcagcag aagaccaagc agaagtaatt      660
tggtgcacag acaagccctt gagaagccaa ccaccagatg ctggacaccc tcttcccatc      720
tgtttctgtg tcttaattgt ctgtagacct tgtaatcagc acattgtcac cccaagccat      780
agtctctctc ttatttgtat cctaaaaata cgtactataa agcttttgtt cacacacact      840
ctgaagaatc ctgtaagccc ctgaattaag cagaaagtct tcatggcttt tctggtcttc      900
ggctgctcag ggttcatctg aagattcgaa tgaaaagaaa tgcatgtttc ctgctcttcc      960
ctcattaaat tgcttttaat tcca                                             984
```

METHOD OF ASSESSING THE RISK OF ATHEROSCLEROSIS

This application claims the benefit of U.S. Provisional Application 60/567,420 filed Apr. 30, 2004 which is incorporated herein in its entirety by reference.

A portion of the disclosure of this patent document contains material which is subject to copyright protection. The copyright owner has no objection to the facsimile reproduction by anyone of the patent document or the patent disclosure as it appears in the U.S. Patent and Trademark Office patent file or records, but otherwise reserves all copyright rights whatsoever.

FIELD OF THE INVENTION

This discovery relates to the use of a biomarker to detect disease. More in particular, this discovery relates to a method of detecting disease using a biomarker in a living human.

BACKGROUND OF THE INVENTION

Coronary heart disease (CHD) is the leading cause of death in humans in the U.S. CHD is so pervasive that more humans die of CHD than from any other disease. CHD is caused by a narrowing of the coronary arteries that supply blood to the heart. Too often, this narrowing tragically results in a heart attack in the victim. Unfortunately, each year about a million Americans have a heart attack and tragically about half or more of these heart attacks are fatal even before the heart attack victim can get to a treatment facility.

Without being bound by theory, in one aspect of early stage of CHD (atherosclerosis), it is believed that plaque or fatty materials build up inside the walls of human arteries (carrying oxygenated blood) along with blood components which are attracted to the plaque or fatty materials and sometimes an atheroma results. Sometimes the fatty buildup or plaque breaks open (i.e. plaque rupture) in a human artery which leads to formation of a clot that seals a defect in the artery but unfortunately restricts blood flow resulting in an acute vascular event. When too little blood reaches the beating heart as a result of this restriction in blood flow, ischemia results.

When ischemia is of a long duration there is generally a resulting heart attack which unfortunately is all too often sometimes fatal. In some situations ischemia disturbs the heart's normal rhythm inducing an abnormal increasingly disruptive rhythm such as malignant ventricular arrhythmia which is also usually destructively fatal. Overall, it is the progressive stenosis of an arterial lumen that is believed to be a major contributing factor to a fatal heart attack results for the victim.

In an effort to combat human heart attacks, medical research strives to identify those individuals pre-attack with a high risk toward atherosclerosis and to identify a preventative or treatment regime for them such as an alternative lifestyle, and to identify drugs which are effective against arterial atherosclerosis.

Difficult challenges are presented in that the process of discovering and developing new pharmaceutical drugs is increasingly expensive and challenging. For example, the average length of time from the discovery of a candidate drug to the time of its U.S. Federal Drug Administration approval has increased. And currently it is estimated that an average of 10,000 or more lead (candidate) compounds must be tested in pre-clinical development for every drug that is finally marketed.

Additionally it is estimated that existing pharmaceutical drugs interact with less than five hundred or so biological targets out of an estimated large number of potential targets (~10,000). If this estimate is correct then, this means that the majority of potential drug targets remain undiscovered using presently available techniques.

Thus, despite rapid and noteworthy advances in medical science in this field, a dire need exists for accurately determining the risk to atherosclerosis to individuals, for alerting such individuals to their existing or developing risk, for providing a treatment regime to an afflicted human and for a method of identifying pharmacological drugs which are therapeutic to preventing or ameliorating dangerous and potentially fatal CHD. Further, it is highly desired to have a sensitive and specific biomarker to assess the extent of atherosclerosis in human arteries.

DETAILED DESCRIPTION OF THE DRAWINGS

Figure 1:
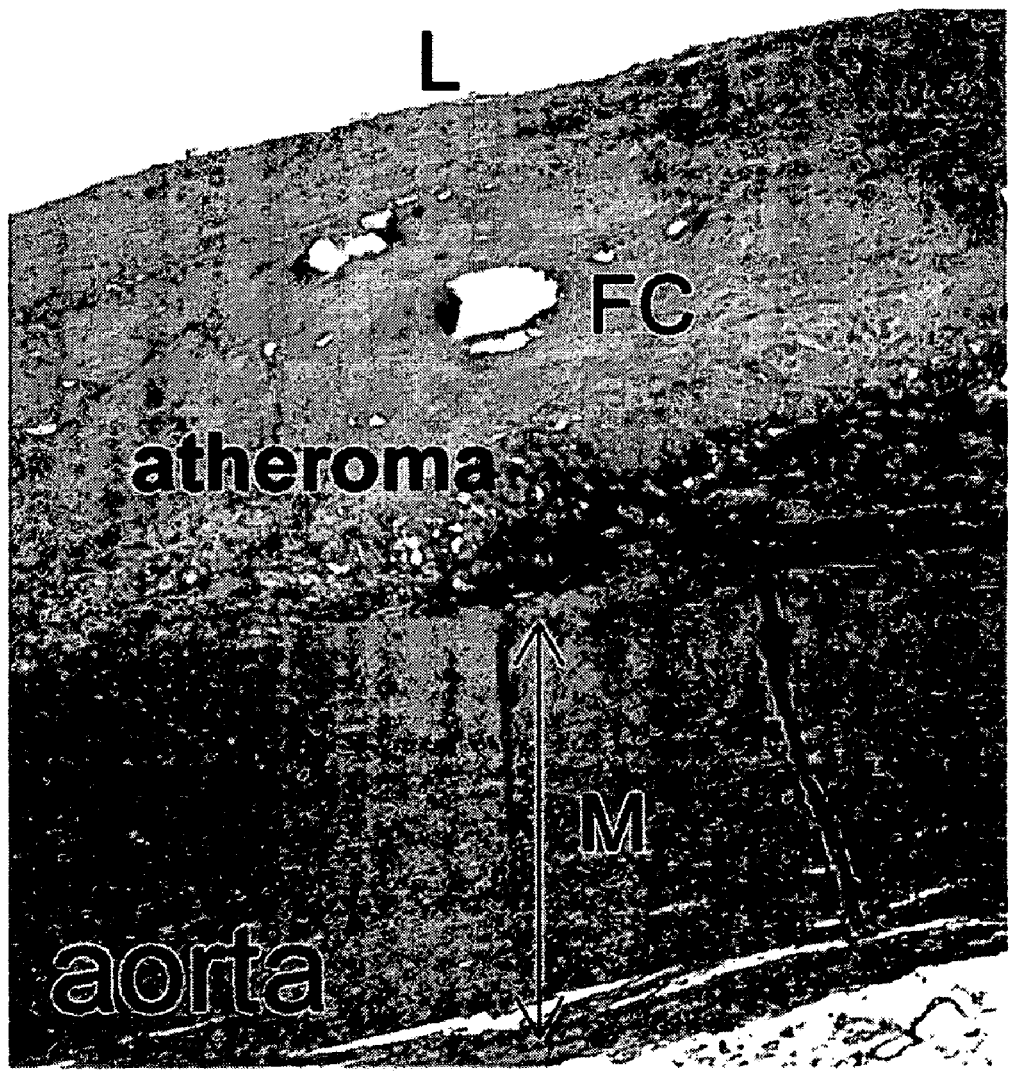
FIG. 1 depicts immunohistochemistry staining of human aorta with specific staining around atherosclerotic plaques.

FIG. 1 depicts immunohistochemistry staining of human aorta. The primary antibody used recognizes human SPRR3 protein. Specific localization of the protein within the vascular wall is visualized by the brown stain deposited when a secondary, chemically-labeled antibody was used to recognize the first anti-SPRR3 (primary) antibody.

Figure 2:
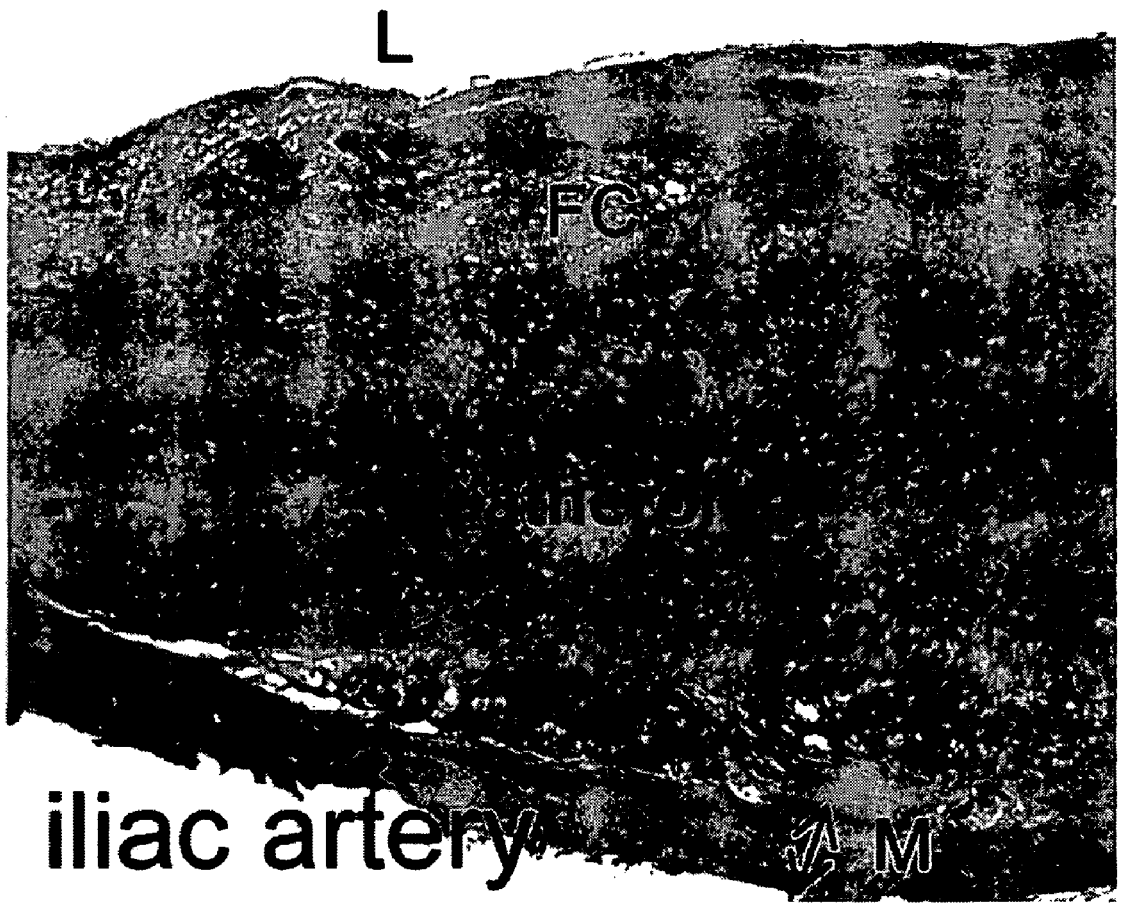
FIG. 2 depicts iliac artery showing extensive staining with SPRR3 particularly around the atheroma.

FIG. 2 depicts iliac artery showing extensive staining by immunohistochemistry with SPRR3 particularly around the atheroma.

Figure 3:
FIG. 3 depicts renal artery with SPRR3 staining within an atheroma.

FIG. 3 depicts human renal artery showing SPRR3 staining within an atheroma.

Figure 4:
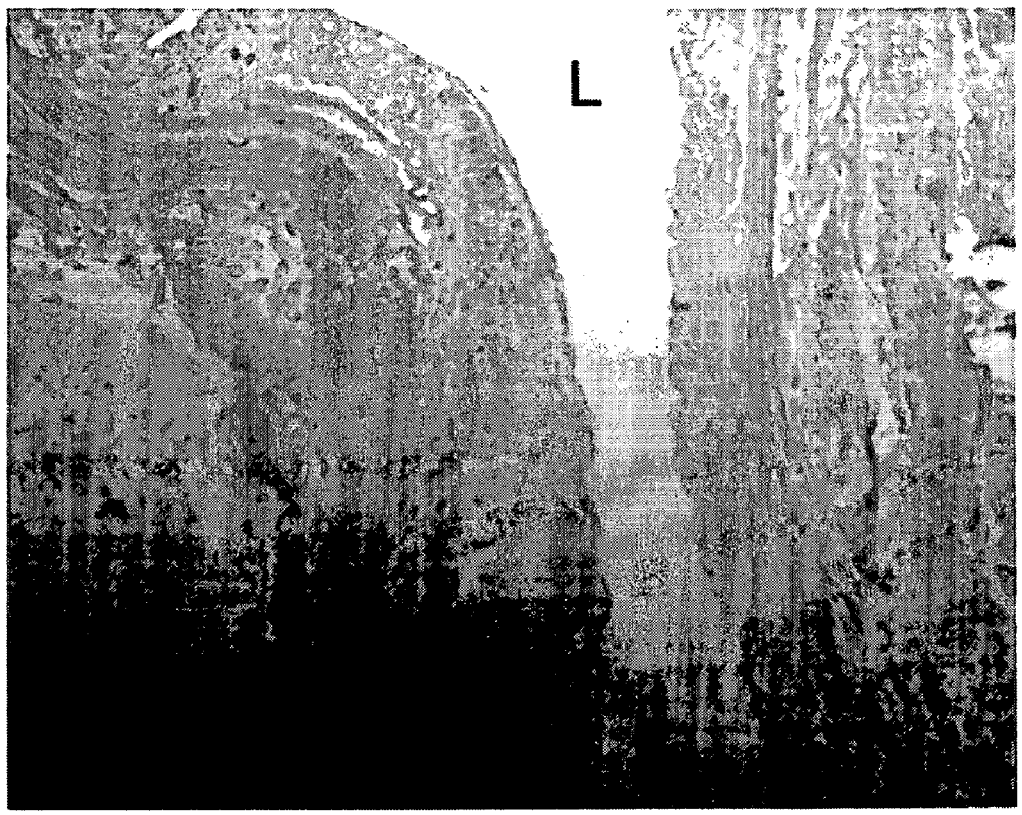
FIG. 4 depicts renal vein which is negative for SPRR3 staining.

FIG. 4 depicts human renal vein which is negative for SPRR3 staining. L, lumen; M, media; FC, fibrous cap.

Figure 5:
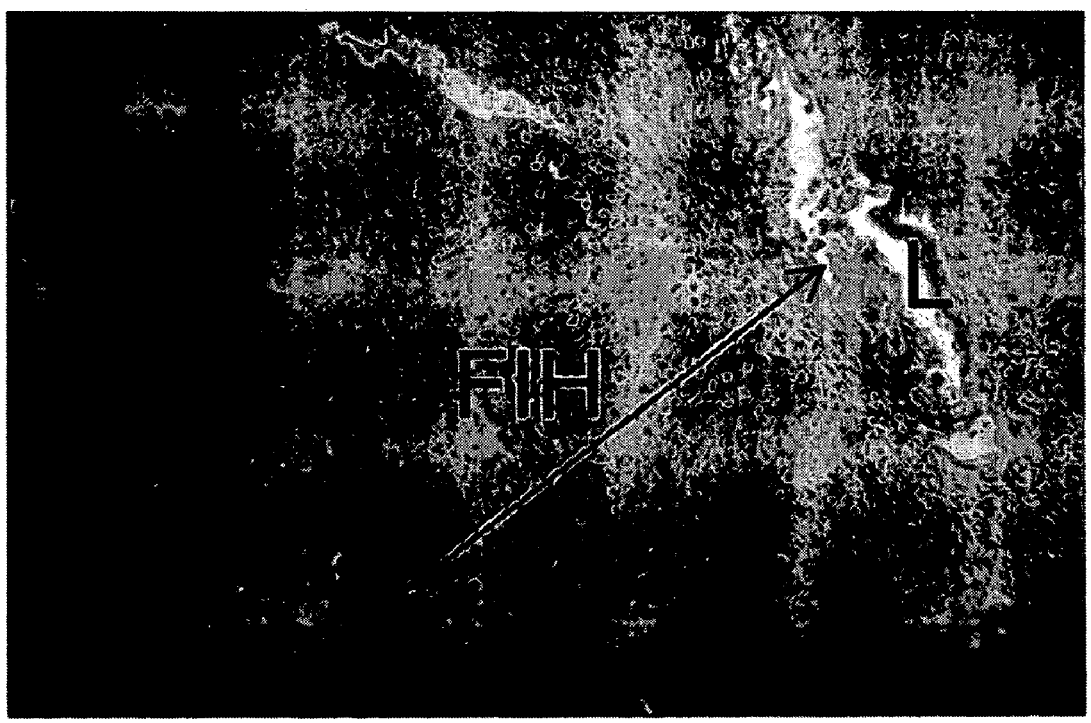
FIG. 5 depicts immunohistochemistry staining of saphenous veins that have been obtained after serving as coronary artery bypass grafts. SPRR3 staining is localized to the region of fibrointimal hyperplasia (FIH) in Panel A.

FIG. 5 depicts immunohistochemistry staining of saphenous veins that have been obtained after serving as coronary artery bypass grafts. SPRR3 staining is localized to the region of fibrointimal hyperplasia (FIH) in panel A.

Figure 6:
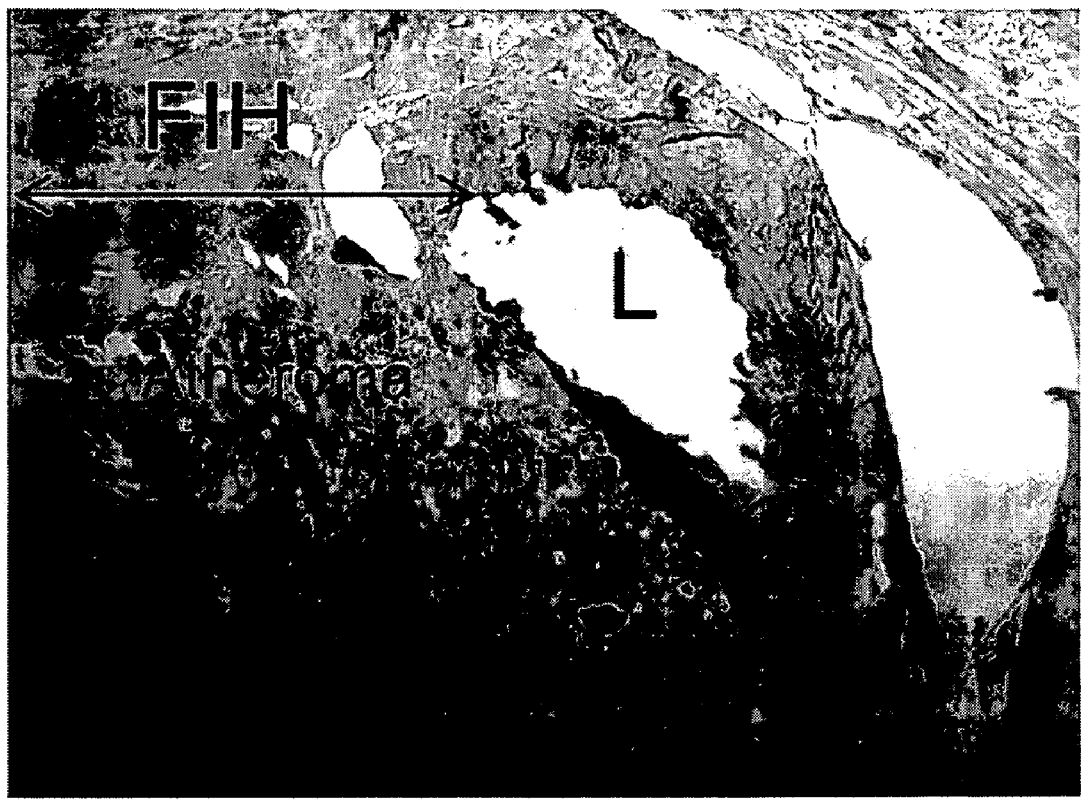
FIG. 6 depicts Panel B showing an advanced atheroma within the FIH with strong SPRR3 staining.

FIG. 6 depicts Panel B shows an advanced atheroma within a saphenous vein arterial graft containing lipid-laden foam cells within the FIH with strong SPRR3 staining of vascular smooth muscle cells and lipid laden foam cells.

Figure 7:
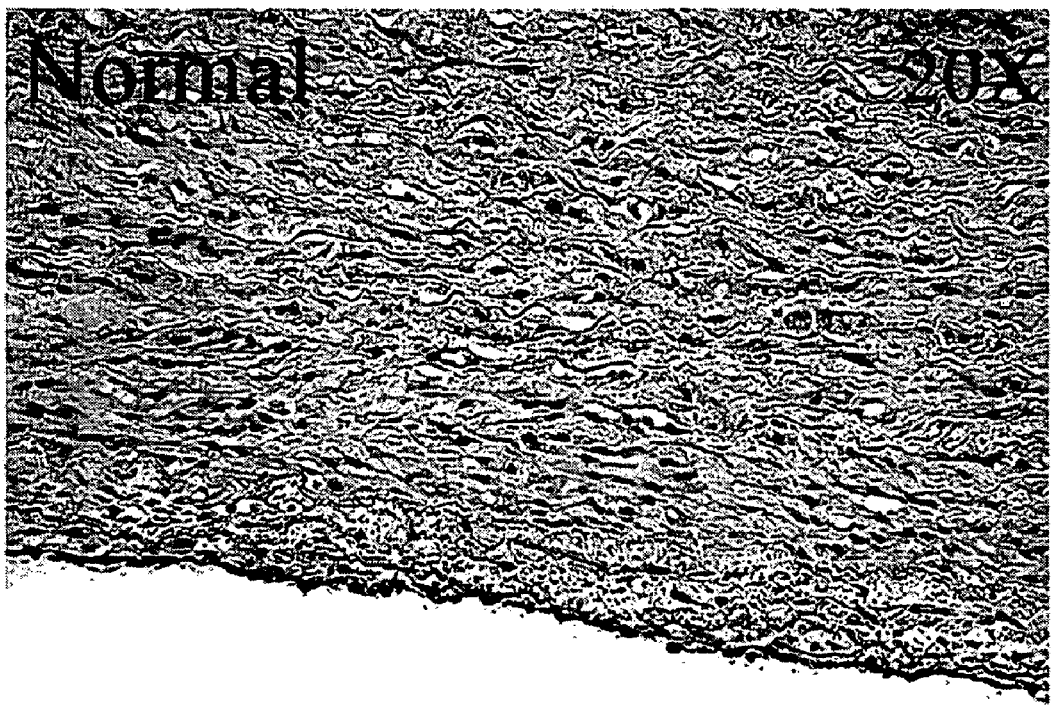
FIG. 7 represents photomicrographs of paraffin sections obtained from autopsy samples from individuals with normal histology (n=11).

FIG. 7 represents photomicrographs of paraffin sections obtained from autopsy samples from individuals with normal histology (n=11).

Figure 8:
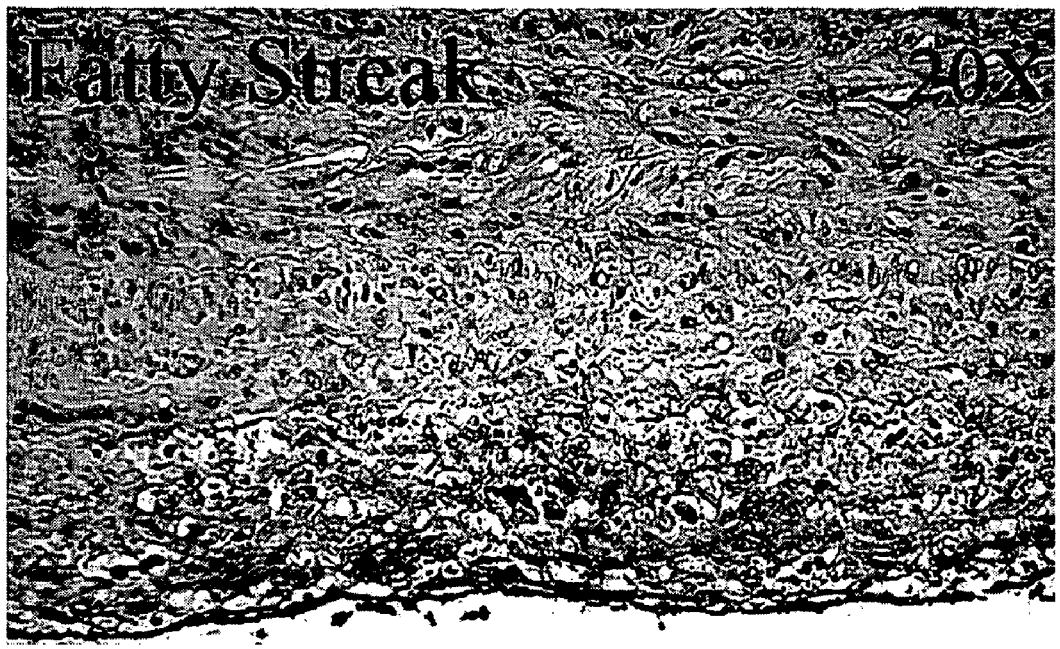
FIG. 8 shows fatty streaks (n=10).

FIG. 8 shows fatty streaks (n=10).

Figure 9:
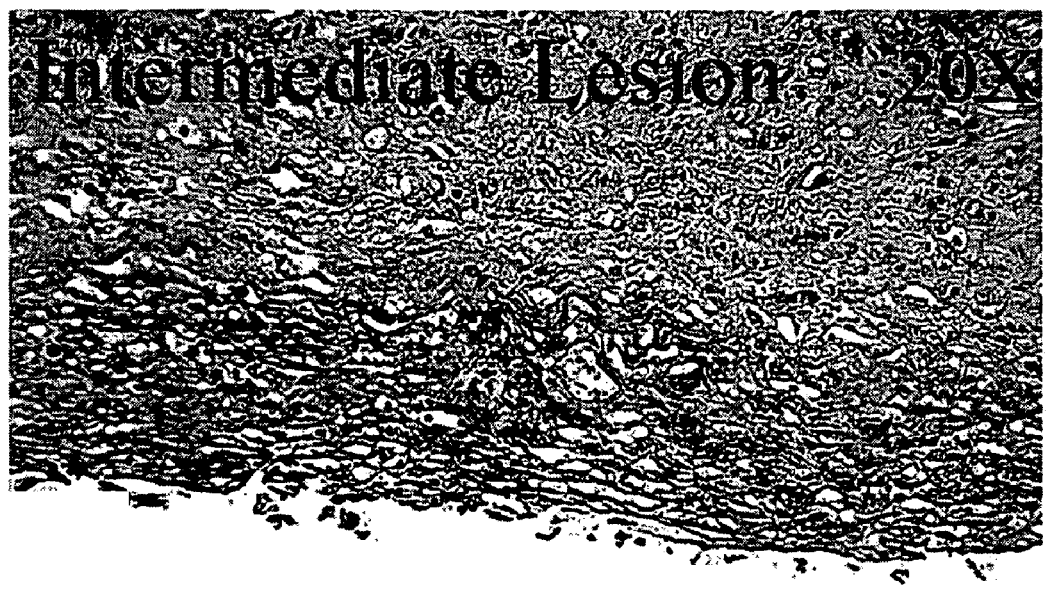
FIG. 9 shows intermediate lesions (n=6).

FIG. 9 shows intermediate lesions (n=6).

SPRR3 was not detected by immunohistochemistry in any normal section. All of the fatty streaks and intermediate lesions (as assessed by histologic examination) stained positive by immunohistochemistry with an antibody to SPRR3.

BRIEF DESCRIPTION OF THE INVENTION

In an aspect, a biological marker useful for specifying the location of biological tissue indicative of atheroma comprises an SPRR3 gene product.

In another aspect, a method for determining whether a human is afflicted with or is likely to be afflicted with atherosclerosis comprises
  (a) determining a level of SPRR3 gene product in a biological sample obtained from the human the level determined by the use of molecular localization,
  (b) comparing the determined level of SPRR3 protein in the biological sample obtained from said individual with a range of SPRR3 levels previously defined as characteristic for humans having atherosclerosis and
  (c) concluding from said comparison that the person is likely afflicted with atherosclerosis when a SPRR3 gene product level is in a range defined as characteristic for the presence of atherosclerosis as an indication that the human is afflicted with atherosclerosis.

In a further aspect, a method of pricing medicine comprises
  (a) determining a level of SPRR3 gene product in a biological sample obtained from a human, the level determined by the use of molecular localization;
  (b) comparing the determined level of SPRR3 gene product in the biological sample obtained from the human with a range of SPRR3 gene product levels previously defined as characteristic for humans having atherosclerosis and
  (c) concluding from this comparison that the human is afflicted with atherosclerosis when a SPRR3 gene product level is in a range previously defined as characteristic for the presence of atherosclerosis as an indication that the human is afflicted with atherosclerosis. In an aspect, the method is non-invasive.

In an aspect, a method of determining the pharmacological activity of a candidate compound towards ameliorating at least one physical manifestation indicative of atherosclerosis in a living human comprises:
  (a) determining the level of SPRR3 gene product by molecular localization in a biological sample obtained from said individual;
  (b) administering a pharmacologically likely effective amount of a candidate drug to the individual,
  (c) determining the level of SPRR3 gene product in a biological sample obtained from an individual by using molecular localization to determine that level, after the passage of an effective time following such administration and
  (d) comparing the determined level of SPRR3 gene product in the vascular sample obtained from the individual with a range of SPRR3 levels previously defined as characteristic for humans having atherosclerosis and using the determination of (c) and
  (e) concluding from said comparison that the drug was effective against atherosclerosis.

In an aspect, a method of providing a therapeutic evaluation of a human for use in determining whether a human is afflicted with atherosclerosis comprises:
  (a) determining the level of a SPRR3 gene product in a vascular sample obtained from the human by using molecular localization technique to determine that level;
  (b) comparing the determined level of SPRR3 gene product in the biological sample obtained from the human with a range of SPRR3 gene product levels defined as characteristic for humans having atherosclerosis,
  (c) constructing a constellation of data for cooperative individuals comprising SPRR3 determined levels and medical data characteristic of individuals having a high risk of atherosclerosis and
  (d) comparing these levels of SPRR3 gene product with the constellation of data. In an aspect, the therapeutic evaluation comprises selecting a therapy to treat the individual based on at least one of constellation medical data and present medical condition and level of SPRR3 gene product.

In an aspect, a database comprises at least one data point comprising the level of SPRR3 gene product in a vascular sample obtained from a human individual by molecular localization after the passage of an effective time based on administering an effective amount of a candidate drug to an individual.

DETAILED DESCRIPTION OF THE INVENTION

This discovery relates generally to a characterized SPRR3 biomarker useful for diagnosing vascular athersclerosis in a living or deceased human and to a diagnostic method of using an SPRR3 gene product as a biomarker for assessing the risk of atherosclerosis in a living human. In particularly this discovery relates to a method of effectively determining the presence of and level of a SPRR3 gene product using molecular localization, a detection technique. More particularly this discovery relates to a diagnostic method of assessing such risk using an SPRR3 biomarker in therapeutical clinical and autopsy environments.

The inventors have discovered a method of accurately assessing the risk to a living human of atherosclerosis using the human gene SPRR3 as a functional biomarker. The inventors' discovery of SPRR3 as a molecular marker for atheroma is the first reported molecular marker for atheroma(s). The inventors have discovered that SPRR3 is a marker for the presence of atherosclerosis and that detection of SPRR3 is helpful in identifying atherosclerotic lesions on its own or as part of a histopathologic evaluation in an aspect. The SPRR3 marker is identified using molecular localization.

We have discovered that the specific expression of SPRR3 gene in the atherosclerotic plaques allows for the levels of SPRR3 in plasma, urine and other body fluids to be predictive of atherosclerotic burden in any given individual. In this manner, the levels of SPRR3 can be used to make medical decision to guide therapy or estimate risk in patients with atherosclerosis. Additionally, changes in SPRR3 levels in response to novel investigational therapies can be used to indicate efficacy.

Further, this discovery comprising use of SPRR3 as a biomarker provides a method of risk assessment of a person having atherosclerosis including atherosclerotic plaque formation. This discovery is useful in clinically identifying a potential therapy or treatment of atherosclerosis to a patient in a clinical setting and a method of identifying a potential therapy for the patient from among several available candidate therapies. This discovery is a direct functional biomarker for the presence of atherosclerosis and is an acceptable functional surrogate for other approaches.

Unless otherwise defined, technical and scientific terms used herein have the same meaning as commonly understood by one of ordinary skill in the art. Methods and materials similar or equivalent to those described herein can be used in the practice or testing of the present discovery.

All publications, patent applications, patents and other references mentioned herein are incorporated by reference in their entirety. In addition, examples are illustrative only and not intended to be limiting in any way.

As used herein, the term "molecular localization" includes the use of any molecule such as RNA (e.g. probe) or protein (e.g. antibody) or small molecules (e.g. molecular radiolabeled tags) to capably detect a SPRR3 gene product(s).

As used herein, the term "molecular localization" is a useful detection technique which encompasses use of antibodies or fragments thereof capable of specifically capably recognizing one or more epitopes of an SPRR3 gene product, epitopes of conserved variants of such SPRR3 gene products, epitopes of mutant gene products or peptide fragment of a SPRR3 gene expression product. Such non-limiting antibodies useful in molecular localization include polyclonal antibodies, monoclonal antibodies, humanized or non-limiting antibodies include conjugated and nonconjugated types.

As used herein, the term "gene product" includes as applied to SPRR3 proteins, protein fragments, peptides, translated nucleic acid, epitopes and polypeptides thereof.

As used herein, the term "peptide" includes any of a group of compounds comprising two or more amino acids linked by chemical bonding between their respective carboxyl and amino groups. The term "peptide" includes peptides and proteins that are of sufficient length and composition to effect a biological response, e.g. antibody production or cytokine activity whether or not the peptide is a hapten. The term "peptide" includes modified amino acids, such modifications including, but not limited to, phosphorylation, glycosylation, pegylation, lipidization and methylation.

As used herein, the term "polypeptide" includes any of a group of natural or synthetic polymers made up of amino acids chemically linked together such as peptides linked together. The term "polypeptide" includes peptide, translated nucleic acid and fragments thereof.

As used herein, the term gene includes "polynucleotide" which includes nucleotide sequences and partial sequences, DNA, cDNA, RNA variant isoforms, splice variants, allelic variants and fragments thereof.

As used herein, the terms "protein", "polypeptide" and "peptide" are used interchangebly herein when referring to a translated nucleic acid (e.g. a gene product). The term "polypeptide" includes proteins.

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form.

As used herein, the term "expression" includes the biosynthesis of a product as an expression product from a gene such as the transcription of a structural gene into mRNA and the translation of mRNA into at least one peptide or at least one polypeptide.

As used here, the terms "isoforms" and "splice variant" includes alternative occurring forms of RNA transcribed from a genome as well as polypeptides encoded by a splice variant of mRNA transcribed from a gene.

As used herein, the term "antibody" includes both an intact or entire antibody, and a useful antibody fragment or epitope. The term "antibody" includes antigen binding forms of antibodies and refers to a polypeptide substantially encoded by an immunoglobulin gene or immunoglobulin genes, or fragments thereof which specifically bind and recognize an analyte (antigen).

As used herein, the term "antibody fragment" is any capably functional useful portion of an antibody, including an epitome, which binds the same antigen (protein comprising a polypeptide that is recognized and capably bound by an intact or nonfragmented antibody.

As used herein, the term "humanized antibody" and ("engineered human antibody") includes recombinant proteins in which murine complementarity determining regions of a monoclonal antibody have been synthetically transferred or exchanged from heavy and light variable chains of the murine immunoglobulin into a human variable domain.

As used herein, the term "therapeutic agent" is any molecule or atom which is conjugated, fused or otherwise affixed to an antibody moiety to produce a conjugate which is useful for therapy.

As used herein, the phrase "specifically (or selectively) binds to an antibody" or specifically (or selectively) reactive with," or recognize when referring to a protein, peptide, or polypeptide refers to a binding reaction that is determinative of the presence of the protein in a heterogeneous population of proteins and other biologics. Thus, under designated immunoassay conditions, specified antibodies bind to a particular protein and do not bind in a significant amount to other proteins which may be present in a sample.

As used herein, the term "immunoconjugate" includes a fused product or conjugate of an antibody component with a therapeutic agent or detectable label therewith.

As used herein, the term "fused antibody" means a recombinant molecule comprising an antibody component and a therapeutic agent. Useful nonlimiting therapeutic agents include immunomodulators and toxins.

As used herein, the term "biological sample" includes vascular tissue or blood, urine or other body fluids.

As used herein, the term "antisense" means a strand of RNA whose sequence of bases is complementary to messenger RNA.

As used herein the term "oligo" includes oligonucleotides which are polymers of nucleosides joined, generally, through phosphoester linkages.

As used herein, the terms "oligonucleotide" and "polynucleotide" are interchangeable and include single-stranded DNA (ssDNA), double-stranded DNA (dsDNA), single-stranded RNA (ssRNA) and double-stranded RNA (dsRNA), modified oligonucleotides and oligonucleosides and combinations thereof. The oligonucleotide can be linearly or circularly configured, or the oligonucleotide can contain both linear and circular segments.

As used herein, the term "siRNA" means short interfering RNA.

As used herein a "therapeutic amount" is an amount of antibody which produces a desired or detectable therapeutic effect on or in a mammal administered the antibody.

As used herein, the term "high risk" means that there is a substantial chance and increased likelihood that the individual (living human) is afflicted with atherosclerosis. "High risk" means that there is the substantial likelihood that one or more forms of atherosclerosis is present in the human's intimae.

As used herein, the term "atherosclerosis" includes thickening and hardening of artery walls or the accumulation of fat, cholesterol and other substances that form atheromas or plaques. In some instances, atherosclerosis is a response to injury in some instances of the intimae of the large and medium sized arteries of the body which are phagocytes forming plaques or atheromas. Whether arising from calcification, hemorrhage, ulceration, thrombosis or trauma, atherosclerosis is undesirably unfortunate.

As used herein, the term "range of values characteristic of an individual having an increased risk of atherosclerosis" includes those medical measurements and analytical data of patient which are shown to be associated with the presence of atherosclerosis in patients. This range is more particularly identified by a region bordered by a low finite value and a high finite value, both values being population variable but determinable.

As used herein, the term "sample" means a viable (analyzable) sample of biological tissue or fluid. A biological sample includes an effective amount of a representative section of tissues or fluids of living animals, viable cells or cell culture.

The inventors have focused on connective tissue sheath around a blood vessel which can be divided into three regions or "tunica". The innermost layer is tunica intimae and is composed of endothelium and connective tissue on the lumenal side of the internal elastic lamina. The tunica intimae of larger vessels is considerably thicker, with the arterial intimae being thicker than in veins. The major cell type in the normal tunica intimae is the intimal smooth muscle cell (SMC). Other cells such as lymphocytes and macrophages may also be present. Proceeding outward lays the tunica media which is composed of SMC layers, followed by the tunica adventitia, a coat of collagen rich connective tissue and fibroblast. Most forms of vascular diseases, from atherosclerosis to iatrogenic injuries, directly affect the vascular intimae and result in intimal thickening (also referred to as fibrointimal hyperplasia or FIH) resulting from SMC proliferation and deposition of extracellular matrix. Atherosclerotic lesions appear to be confined to the intimae.

The inventors have identified (using gene array analysis) a number of genes that are expressed selectively in the mouse aorta but not in the mouse inferior vena cava (IVC). The inventors have used antibodies successfully against a protein expressed from SPRR3 gene and have shown that expression of the SPRR3 protein is restricted to the intimae of the human artery. By quantitative RT-PCR analysis the inventors have determined by evidence that this protein is expressed in significantly higher levels in arterial biopsy samples than in IVC.

SPRR3 is a well known isolated and characterized human small proline—rich protein 3 which is an SPRR3 gene product. The SPRR3 protein and messenger RNA sequences are known and are publicly accessible at. The SPRR3 gene is located within a cluster of 1.5 Mbp on human chromosome 1q21.

The protein sequence (SEQ ID NO:1) is

```
  1 mssyqqkqtftpppqlqqqq vkqpsqpppq eifvpttkep chskvpqpgn tkipepgctk
 61 vpepgctkvp epgctkvpep gctkvpepgc tkvpepgctk vpepgytkvp epgsikvpdq
121 gfikfpepga ikvpeqgytk vpvpgytklp epcpstvtpg paqqktkqk
```

The mRNA sequence (SEQ ID NO:2) is:

```
  1 accagatccc agaggctgaa cacctcgacc ttctctgcac agcagatgat ccctgagcag
 61 ctgaagacca gaaaagccac taagactttc tgcttaattc aggagcttag aggattcttc
121 aaagagtgtg tccacgatcc tttgaagcat gagttcttac cagcagaagc agacctttac
181 cccaccacct cagcttcaac agcagcaggt gaaacaaccc agccagcctc cacctcagga
241 aatatttgtt cccacaacca aggagccatg ccactcaaag gttccacaac ctggaaacac
301 aaagattcca gagccaggct gtaccaaggt ccctgagcca ggctgtacca aggtccctga
361 gccaggctgt accaaggtcc ctgagccagg ttgtaccaag gtccctgagc aggctgtac
421 caaggtccct gagccaggtt gtaccaaggt ccctgagcca ggctacacca aggtccctga
481 accaggcagc atcaaggtcc ctgaccaagg cttcatcaag tttcctgagc caggtgccat
541 caaagttcct gagcaaggat acaccaaagt tcctgtgcca ggctacacaa agctaccaga
601 gccatgtcct tcaacggtca ctccaggccc agctcagcag aagaccaagc agaagtaatt
661 tggtgcacag acaagccctt gagaagccaa ccaccagatg ctggacaccc tcttcccatc
721 tgtttctgtg tcttaattgt ctgtagacct tgtaatcagc acattgtcac cccaagccat
781 agtctctctc ttatttgtat cctaaaaata cgtactataa agcttttgtt cacacacact
841 ctgaagaatc ctgtaagccc ctgaattaag cagaaagtct tcatggcttt tctggtcttc
901 ggctgctcag ggttcatctg aagattcgaa tgaaagaaa tgcatgtttc ctgctcttcc
961 ctcattaaat tgcttttaat tcca
```

For the proteins expressed by the SPRR3 gene, such expression was noted to be discontinuous within the intime by the inventors and hence was further examined by histochemistry by the inventors to further localize expression within the vessel intimae. Examination of multiple arteries gave evidence leading to this discovery that the protein expressed from the SPRR3 gene is significantly closely associated with atherosclerotic plaques (FIG. 1). Expression of SPRR3 was not detected in several venous samples such as pulmonary vein, renal vein, superior vena cava, and coronary vein FIG. 1).

The inventors discovered that SPRR3 protein is relevant in the biomechanical role of the arterial intimae as the inventors believe that SPRR3 gene product expression is upregulated with venous arterialization which happens when a vein is interposed into the arterial circulation such as in coronary artery bypass surgery (CABG). These grafts of CABG are also predisposed to atherosclerosis, a disease typically restricted to arterial intimae. Several saphenous vein coronary grafts were obtained from post mortem samples and examined by histochemistry for SPRR3 expression. The inventors found that SPRR3 was upregulated in several regions of fibrointimal hyperplasia and regions of atherosclerosis in these grafts (FIG. 2). While atherosclerosis is limited to arteries, it also occurs with high frequency in arterialized veins and is part of the pathophysiology that leads to failure at times of venous grafts.

In an aspect, illustrative useful monoclonal antibodies useful in molecular localization are obtained by any technique which provides for the production of antibody molecules by continuous cell lines in culture.

Illustrative useful polyclonal antibodies in molecular localization includes those which are derived from the sera of animals immunized with an antigen such as a SPRR3 gene product or an antigenic function derivative. For the production of polyclonal antibodies living, host animals such as those previously described may be immunized by injections with SPRR3 gene product or fragments thereof, and optionally supplemented with effective adjuvants to enhance expression.

Immunohistochemistry is a viewable valuable quantification technology useful to detect the location and relative abundance of a protein using an antibody which binds to that protein. The main aspect of immunohistochemistry technology is to provide the capacity to visually identify the location of the antibody after it is bound to the protein. Thus, identifying the location of the protein.

For example, as applied herein, in an aspect a first antibody is generated in a mouse and binds to a protein product expressed by the SPRR3 gene. A secondary antibody is employed that binds to mice antibodies and has at least one of a chemical and/or fluorescent dye covalently attached to that antibody. The second antibody can capably bind to multiple sites on the primary antibody thus providing a brighter human eye visible signal providing the location of the SPRR3 gene product.

In practicing an aspect of this discovery using molecular localization one can use an antibody specific for a SPRR3 gene product in a diagnostic test to detect the presence of the expressed SPRR3 gene product (protein) in body tissue or fluids. In particular the SPRR3 gene product will express itself in intimae when there is an increased risk of atherosclerosis presented in the living human intimae. Molecular localization provides the detection of that expression.

In another aspect the present discovery comprises use of the SPRR3 gene product(s) in an analysis of its expression for the identification of potentially therapeutic compounds which could prevent, ameliorate, reduce atherosclerosis or cause its retardation or regression in a living mammal such as in a living human. In such an aspect through molecular localization one can detect the presence and level of SPRR3 gene expressed product(s) and after administration of a potentially therapeutic compound, one can reliably detect the presence and level of SPRR3 gene expressed product(s). One can then compare the level of SPRR3 before and after such administration to determine whether there has been any change in the SPRR3 level. If such a comparison shows no change or an increase in SPRR3 level detected after administration, then the compound is determined to not be of value in reducing or ameliorating atherosclerosis. If such a comparison shows a reduced level of SPRR3 then the compound is determined to be of value in reducing or ameliorating atherosclerosis.

In another aspect, this invention is employed to characterize the staging of the atherosclerosis in a human patient. This is useful for selecting a recommended treatment regime for individual patients, estimating prognosis and comparing the results of different therapy programs.

In one aspect of practicing this invention, a series of data points are taken of the level of SPRR3 gene product in a living sample of tissue or body fluid using this discovery along with other data representative of whether the human supplying the sample had atherosclerosis. In an aspect the data are assembled in a database comprising arrays of data correspondingly linked in the database. The series of data points is added to and stored in an array (database) where regions of the data base are denoted as data from individuals having atherosclerosis or being at high risk for having atherosclerosis. In this manner, the data base provides a baseline or range of SPRR3 levels from individuals previously defined as characteristic for the presence of atherosclerosis as an indication that the individual is so afflicted.

In an aspect, this invention is useful to provide disease prevention including being able to put on notice an individual to take steps to ensure good heart health before a fatal or disabling heart event occurs. Knowledge that a SPRR3 level is high provides a practitioner with the capability to place a human on notice that he/she has an elevated risk of heart disease. This should enable the patient, such as a living human, to reduce that risk.

In an aspect, this discovery is useful in a method for determining the anatomic extent of such atherosclerosis, its progression and for enhanced assessment of the risk of such atherosclerosis. The inventors discovered that SPRR3 gene product is an effective biomarker which is a predictor (or suspicion indicator) of the presence or future occurrence of atherosclerosis which can increase the risk of myocardial infarction and/or stroke. This discovery is quite useful in making difficult clinical decisions such as whether to use and which therapies to use in a preventative treatment especially when such available evidence to determine such therapies is lacking and as such is useful in combination with other diagnostic procedures. This discovery is also believed useful in the identification of antithrombotic agents which are those agents which prevent the formation of thrombus with undesired accompanying myocardial infarction.

An autopsy provides an analytical opportunity to determine the cause of the death of an individual but also to add to the body of knowledge as regards a lethal disease such as atherosclerosis. In an autopsy, the heart and the aorta and major branches (renal, celiac, mesenteric, and iliac arteries) are opened longitudinally and visible and physically examined. Measurements may be made if desired on the preserved tissue.

In an aspect, this discovery is practiced during an autopsy. During this procedure (a histopathologic evaluation) a pathologist examines the heart, removes it from the body and generally the first step following its removal is sectioning the coronary arteries that supply the heart with blood. In an aspect, an examination is also done of the carotid arteries. (There is often arterial disease here, even in unsuspecting living people.) The autopsy processing involves fixation, dehydration, embedment and subsequent sectioning with a microtome of the desired tissue. In an aspect histochemistry is employed to examine thin slices of intimae prepare of the aorta, which are sufficiently thin to allow light to pass through the slices.

The level of SPRR3 gene product expression may be determined in accordance with this discovery using an appropriate and useful sample of the preserved intimae in the autopsy. The level of expression may be correlated to the visual determination of the extent of atherosclerosis presented during the autopsy. In this manner, using data from SPRR3 gene product expression and visual observations, the pathologist is able to establish an atherosclerosis index based on the association of the expression of SPRR3 with atherosclerosis which is linked to the individual if desired.

In an aspect the pathologist saves an effective useable amount of a sample as a section in preservative solution and submits the tissue to the histology lab, to be made into microscopic slides. In an aspect a determination is made of the level of SPRR3 gene product using molecular localization on that sample by effectively contacting the sample with an antibody recognizing an SPRR3 gene product either as a naked antibody or as an antibody conjugated with a radiolabel or a chemical dye. In a further aspect a second antibody may be contacted with the sample after the first antibody has been contacted therewith. After a sufficient time of contacting has passed the slides are ready and are visually examined (histochemical staining) or subjecting to a radiation detector. This enables a conclusion to be drawn as to the level of SPRR3 gene product via molecular localization technique. Advantageously the data from the autopsy and the determination of the level of SPRR3 gene product obtained by molecular localization are employed to further enhance the knowledge of the discovered association between the level of SPRR3 gene product in intimae and atherosclerosis.

In another aspect the level of SPRR3 gene product is determined in a living human (patient) initially at a singular instance such as an initial early age and which may be conveniently repeated several times at various convenient intervals over the passage of time. For example, the level of SPRR3 gene product is determined in a twenty year old living human and thereafter at selected time intervals, for example, every five or so years thereafter for at least two or more time intervals. The level of SPRR3 gene product is data which is retained. The interval selected is typically a time passage following a first time determination of SPRR3 gene product such that any possible damage had an opportunity to occur and be meaningful. In this manner a "SPRR3 gene product expression profile" as a function of the passage of time for that individual is generated and is useful as a predictor of the onset or progression of atherosclerosis in that human.

More particularly in this regard, the level of determination may be carried out by injecting the human with an antibody recognizing an SPRR3 gene product. Further in this regard the antibody may itself be considered a primary antibody, i.e. an antibody which recognizes and binds to the SPRR3 gene product. Another antibody may be employed cooperatively with the first antibody, the second antibody recognizing the first antibody and being a reporter type antibody such as a radiolabelled antibody. An example of a useful two antibody type system comprises a rabbit antibody as a primary antibody and a goat anti-rabbit antibody as a second antibody. In an aspect the goat anti-rabbit antibody is radiolabelled.

Further in that regard the reporter antibody is appropriately radiolabelled so that a corresponding radiolabel detector would capably identify a pattern for the location of any radiolabelled antibody recognizing SPRR3 gene product. Depending on the degree of any localization or patterning of the radiolabel, the attending physician would be able to classify such localization or patterning as indicative of the degree of atherosclerosis presented at that time in the human patient without biopsying the patient.

In an aspect, monoclonal and polyclonal antibodies are prepared that react with i.e. recognize a SPRR3 gene product comprising a polypeptide having a sequence disclosed as noted in paragraph 72 aforegoing, in accordance with accepted laboratory practice. (A useful Monocolonal antibody production is described in Monoclonal Antibody Production, A Report of the Committee on Methods of Producing Monoclonal Antibodies Institute for Laboratory Animal Research National Research council, National Academy Press, Washington D.C. 1999 which is incorporated herein by reference in its entirety.)

Antibodies useful herein can be prepared by immunizing various host living animal by injection with an SPRR3 gene product or a sufficiently functional fragment thereof. Fragments of SPRR3 can be synthesized as antigenic peptides in accordance with the known amino acid sequence of SPRR3. Adjuvants may be employed to increase the immunological response including but not limited to Freund's complete and incomplete, mineral gels, emulsions and potentially useful human adjuvants such a BCG and *Corynebacterium parvum*.

In an aspect, monoclonal antibodies are produced in a mouse which is immunized by injection of an appropriate antigen to stimulate the production of antibodies targeted against that antigen in the mouse. (see Kohier & Milstein, *Eur. J Immunol.* 6:511-519 (1976)).

Further in this aspect, the antibody forming cells are isolated (i.e. harvested) from the mouse's spleen. Monoclonal antibodies (hybridomas) are produced by fusing the single antibody-forming cells to eternal tumor (cancer) cells grown in culture.

Alternative methods of immortalization include transformation with Epstein Barr Virus, oncogenes, or retroviruses, or other methods well known in the art. In an aspect, colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

After reading this specification those of skill in the art will recognize methods of producing polyclonal and monoclonal antibodies that can react specifically with SPRR3 gene product (see, e.g., Coligan, *Current Protocols in Immunology* (1991); Harlow & Lane, supra; Goding, *Monoclonal Antibodies: Principles and Practice* (2d ed. 1986); and Kohier & Milstein, *Nature,* 256:495497 (1975) and (see, e.g, Huse et al., *Science* 246:1275-1281 (1989); Ward et al., *Nature* 341: 544-546 (1989)) would be useful in practicing this discovery.

In an aspect an immunogen is used to produce antibodies that specifically reactive with SPRR3 gene product. For example, recombinant SPRR3 gene product or a antigenic fragment thereof such as the core or tail domain, is isolated. A recombinant protein can be expressed in eukaryotic or prokaryotic cells, and purified using a vector and a host cell. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies.

More in detail, various methods of general production of polyclonal antibodies known to those of skill in the art may be employed hereinafter reading the specification. For example, an inbred strain of mice or rabbits is immunized with the protein using a standard adjuvant, such as Freund's adjuvant, and a standard immunization protocol. The animal's immune response to the immunogen preparation is monitored by taking test bleeds and determining the titer of reactivity to SPRR3 gene product. When appropriately high titers of antibody to the immunogen are obtained, blood is collected from the animal and antisera are prepared. Further fractionation of the antisera to enrich for antibodies reactive to the protein can be done if desired (see Harlow & Lane, supra). In as aspect, monoclonal antibodies and polyclonal sera are collected and tittered against the immunogen protein SPRR3 gene product in an immunoassay, for example, a solid phase immunoassay with the immunogen SPRR3 gene product immobilized on a solid support. In an aspect, polyclonal antisera with a titer of $10^4$ or greater are selected and tested for their cross reactivity against non-SPRR3 gene product proteins or even other homologous proteins from other organisms, using a competitive binding immunoassay.

For a review of immunological and immunoassay procedures, see *Basic and Clinical Immunology* (Stites & Terr eds., 7th ed. 1991). Moreover, the immunoassays of the present discovery can be performed in any of several configurations, which are reviewed extensively in *Enzyme Immunoassay* (Maggio, ed., 1980); and Harlow & Lane, supra.

In this regard, antibodies or fragments thereof may be used to qualitatively and quantitatively detect, by molecular localization, the presence of SPRR3 gene products or conserved variants or peptide fragments thereof.

For example, the antibodies or fragments thereof may be employed histologically for in situ detection of the SPRR3 gene product(s). In an aspect such detection is accomplished by removing a histological sample or specimen from a living human. The amount of SPRR3 gene product is assess by molecular localization such as immunohistochemistry Such approaches will involve incubating an effective amount of a sample such as of intimae including a fresh tissue extract, freshly harvested cells or lysates of cells which have been incubated in cell culture.

More particularly in this regard, molecular localization may be effectively carried out by injecting the human with an antibody recognizing at least one SPRR3 gene product. Further in this regard the antibody may itself be considered a first antibody, i.e. an antibody which recognizes and binds to the SPRR3 gene product.

The first antibody may be used itself to identify the SPRR3 gene product (i.e. conjugate antibody) as by having a reporter functionality associated with it such as a chemical stain capability or a detectable radiolabel.

Alternately another antibody may be employed cooperatively with the first antibody in the event the first antibody is nonconjugate, the second antibody recognizing the first antibody and being a reporter type antibody such as a chemical staining or radiolabelled antibody.

A useful illustrative two antibody "tandem type" antibody system comprises a rabbit antibody as a primary antibody and a goat anti-rabbit antibody as a second antibody. In an aspect the goat anti-rabbit antibody is radiolabelled.

Further in that aspect the conjugate reporter antibody is appropriately radiolabelled so that a corresponding radiolabel detector would capably identify a pattern for the location of any radiolabelled antibody recognizing SPRR3 gene product thus providing the location of the SPRR3 gene product. Depending on the degree of any localization or patterning of the radiolabel, a physician would be able to classify such localization or patterning as indicative of the degree of atherosclerosis presented at that time in the human patient without necessarily biopsying the patient.

Conjugated monoclonal and conjugated polyclonal antibodies are especially useful herein in that they can be used for administering an effective amount of radiolabeled antibody comprising a conjugated antibody binding to a desired tissue locus presenting as a target thereto a SPRR3 gene product.

Conjugated antibodies include those antibodies which are joined to a chemically active dye or a radioactive particle.

Useful nonlimiting conjugated monoclonal antibodies include those antibodies that are individually joined to radioactive atoms or chemical stainers, and used as delivery vehicles to transport chemicals and radioactive atoms via the mammalian vascular system. Conjugated antibodies MAbs are also sometimes referred to as conjugated MAbs, and "tagged," "labeled," or "loaded.

MAbs with radioactive particles attached are referred to as radiolabeled. Such radiolabeled antibodies can be used to detect areas of atherosclerosis spread in the body as detectable functional radionuclides.

If desired, the radiolabels are incorporated into nucleic acids for use in detecting SPRR3 gene product such as mRNA. This can be done by any of a number of ways apparent to those of skilled in the art after reading the specification.

Alternatively, a label may be added directly to an original nucleic acid sample (e.g., mRNA, poly $A^+$ mRNA, cDNA, etc.) or to the amplification product after the amplification is completed. Means of attaching labels to nucleic acids are well known to those of skill in the art and include, for example, nick translation or end-labeling (e.g., with a labeled RNA) by phosphorylation of the nucleic acid and subsequent attachment (ligation) of a nucleic acid linker joining the sample nucleic acid to a label (e.g., a fluorophore).

The particular label or detectable group used in the assay is not a critical aspect of the invention, as long as it does not significantly interfere with the specific binding of the antibody used in the assay.

Non-radioactive chemical staining (dye) labels are often attached by indirect means. Generally, a ligand molecule (e.&, biotin) is covalently bound to the molecule. The ligand then binds to an anti-ligand (e.g., streptavidin) molecule which is either inherently detectable or covalently bound to a signal system, such as a detectable enzyme.

Means of detecting such labels are well known to those of skill in the art. Thus, for example, radiolabels may be detected using photographic film or scintillation counters. Enzymatic labels are typically detected by providing the enzyme with a substrate and detecting the reaction product produced by the action of the enzyme on the substrate, and colorimetric (dye) labels are detected by simply visualizing the colored label.

Any metallic radioisotope capable of being detected in a diagnostic procedure can be employed to prepare a functional radionuclide. For example, suitable radioisotopes include:

Antimony-124, Antimony-125, Arsenic-74, Barium-103, Barium-140, Beryllium-7, Bismuth-206, Bismuth-207, Cadmium-109, Cadmium-115 m, Calcium-45, Cerium-139, Cerium-141, Cerium-144, Cesium-137, Chromium-51, 152, Gadolinium-153, Gold-195, Gold-199, Hafnium-175, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195 m, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110 m, Silver-111, Sodium-22, Strontium-85, Strontium-89, Strontium-90, Sulfur-35, Tantalum-182, Technetium-99 m, Tellurium-125, Tellurium-132, Thallium-204, Thorium-228, Thorium-232, Thallium-170, Tin-113, Titanium-44, Tungsten-185, Vanadium48, Vanadium49, Ytterbium-169, Yttrium-88, Yttrium-90, Yttrium-91, Zinc-65, and Zirconium. Technetium-99 m may be useful for SPECT imaging studies. Rhenium-188, rhenium-186, copper-64 and yitrium-90 may be useful.

In an aspect, the antibody is incorporated in a pharmaceutic composition suitable for administration to a living mammal. One or more antibodies may be so incorporated. Useful antibodies include naked and conjugated monoclonal and polyclonal conjugated antibodies.

In an aspect, antibody compositions comprising naked monoclonal and polyclonal antibodies and conjugated monoclonal and polyclonal antibodies are employed in the form of pharmaceutical preparations.

In an aspect, the carrier can also contain other pharmaceutically-acceptable excipients and additives for modifying or maintaining pH, osmolarity, viscosity, clarity, color, sterility, stability, rate of dissolution, or odor of the formulation. Similarly, the carrier may contain still other pharmaceutically acceptable excipients for modifying or maintaining release or absorption or penetration.

It is also contemplated that some formulations are more conveniently administered orally. Such formulations are preferably encapsulated and formulated with suitable carriers in solid dosage forms.

The effective amount of such antibody administered must be determined empirically.

Parenteral routes of administration to mammals for such pharmaceutical compositions include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to, pharmaceutically acceptable sterile isotonic solutions.

Diagnosis and treatment are important aspect of this invention. In an aspect, Positron Emission Tomography, (PET) and SPECT are useful diagnostic imaging standard medical procedures that during data acquisition produce (i.e. capture and optionally record) images of the body's biological functions and in an aspect, are used to determine the extent of malignant disease as part of the hyperthermia immunotherapy regime. In an aspect, these imagining procedures show the presence and distribution of a radiolabeled detectable functionally emitting radiolabeled chemical i.e. a radionuclide which is also referred to as PET or SPECT radioligand.

In an aspect, positron emission tomography (PET imaging comprises detection of x-rays emitted from radionuclides that decay by positron emission and are located within the mammalian patient's body. In an aspect, PET is carried out over a time period referred to as a time course.

In an aspect, single photon emission computed tomography (SPECT imaging) comprises a collimation of gamma rays emitted by a radiopharmaceutical distribution such as detectable radioactivity emitting radiological activity within the mammalian body undergoing treatment and analysis. Generally collimators for SPECT imaging are lead and comprise thousands of various shaped parallel channels through which—and only through which—gamma rays are allowed to pass. Generally such collimators are positioned over a single crystal of NaI contained in the Gamma camera in an arrangement called an Anger camera. The image from the camera is the captured image which is presented to a human operator as part of the image in an acquisition process.

In an aspect, a PET and a SPECT image is taken of (i.e. an acquisition is made) a human after administration of a radiolabeled antibody to the mammal.

In an aspect, an emitting radioactive substance is produced in a process and is attached, or tagged, to an antibody as a conjugated antibody which is termed labeling or radiolabeling. Once this radioactive is administered to a human patient, emitted radioactivity localizes in the appropriate areas of the body and is detected by PET scanner or SPECT instrument.

In an aspect, images are taken over elapsed time in a dynamic fashion to assemble a developing or developed scenario of situations in a human patient.

Typically an adequate and effective amount of time is allowed to elapsed for the treated mammal to come to an equilibrium state following satisfactory administration of the pharmaceutical composition comprising a radioligand. Typically the mammal is placed in a position near the PET instrument or SPECT instrument allowing satisfactory operation of the PET instrument and/or SPECT instrument. The PET and SPECT in instruments are equipped with all necessary operable software and operation requirements. They are turned on by supplying 100 volts electric power to the instruments.

Generally after having received its administration of the radiolabeled antibody the mammal is ready for an imaging examination and is taken to an examination room that houses the PET scanner, which has an opening in the middle. In the PET scanner there are multiple rings of detectors that record the emission of energy from the radioactive substance now within in the mammal. In an aspect, the mammal is moved into the hole of the machine. In an aspect, images are obtained of the mammal as part of this radiological examination and are displayed on the monitor of a computer, suitably equipped and operably coupled to the PET scanner instrument. In an aspect, a pharmacologic assessment is made of the imaged locus of tissue.

The specific mammalian dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. The amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Humanizing Monoclonal Antibody Therapy (Engineered human antibody) may be employed. In an aspect a human engineering antibody is prepared following standard laboratory procedure and is administered to a living mammal as a pharmaceutical composition.

Briefly an antibody to SPRR3 is prepared as aforedescribed except that the part of the mouse antibody gene responsible for recognizing a specific tumor antigen (SPRR3) is exchanged with other parts from a human antibody gene. The product of this mouse-human antibody gene, called a "humanized" monoclonal antibody, looks sufficiently like a normal human antibody to avoid being destroyed by the human patient's own immune system.

In an aspect, molecular localization is a detection process that allows systemic use of immuno-technology treatment to the whole mammalian body. In an aspect, the immuno-treatment is targeted which means that the immunotherapy is aimed at SPRR3 gene products.

In an aspect, it is believed that siRNA designed according to the sequence of the gene comprising a SPRR3 gene product for example the siRNA is useful to silence the gene expression in cells containing SPRR3 genes.

In an aspect, treatment is carried out using siRNA at normal mammal body temperature. In an aspect, a gene or genes may be selectively employed to silence silenceable genes using small pieces of RNA called siRNA (short interfering RNA).

Antisense oligodeoxynucleotides (ODNs) or "oligos" are synthetic polymers: having e.g. monomers which are deoxynucleotides like those in DNA.

The construction of a suitable vector can be achieved by any of the methods well-known in the art for the insertion of exogenous DNA into a vector, see Sambrook et al., 1989, Molecular Cloning, A Laboratory Manual, Cold Spring Harbor Press, N.Y.; Rosenberg et al., Science 242:1575-1578 (1988); Wolff et al., PNAS 86:9011-9014 (1989). For Systemic administration with cationic liposomes, and administration in situ with viral vectors, see Caplen et al., Nature Med., 1:39-46 (1995); Zhu et al., Science, 261:209-211 (1993); Berkner et al., Biotechniques, 6:616-629 (1988); Trapnell et al., Advanced Drug Delivery Rev., 12:185-199 (1993); Hodgson et al., BioTechnology 13:222 (1995).

Those of skill in the art will recognize that temperatures and reaction conditions are such to carry out and thus achieve the benefit of this discovery.

The following examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the discovery since various changes and modifications within the spirit of the discovery will become apparent to those skilled in the art from this detailed description. In the following examples, which illustrate the invention, and throughout the specification, parts and percent are by weight unless otherwise indicated.

EXAMPLES

Materials and Methods

RNA isolation and cDNA synthesis: Vascular tissue was obtained from six C57BL/6 mice (Jackson Labs), age 4-8 weeks, by carefully dissecting the aorta (aortic arch to thoracic aorta) and IVC (the segment between the right atrium to just superior to the liver). The vessels were dissected free of periadventitial fat. Various other tissues, including liver, spleen, kidney, brain, skeletal muscle, lung, pancreas, heart and skin were also obtained from 2-6 separate sets of C57BL/6 mice, flash frozen and processed to isolate RNA. Total RNA was isolated utilizing TRIzol LS reagent (Invitrogen). Integrity of the RNA was confirmed by RNA with an A260/A280-ratio>1.9 and 28S/18S ratio of >1.4 (Agilent 2100 Bioanalyzer RNA 6000 LabChip kit).

Microarray analysis: From the total RNA, biotinylated cRNA probes were generated, fragmented and applied as described to Mouse MU74A (Version 2) GeneChip arrays for aorta, skin, IVC, and heart and Version 1 was used for other tissues (Affymetrix, Santa Clara, Calif.). The overall fluorescence intensity across each chip was scaled to 1500 and comparisons of the levels of transcripts were performed with Affymetrix analysis software, Microarray Suite 5.0. The probe sets that were called present using the call metric by the Affymetrix analysis software were selected and subsequently analyzed using Spotfire software. Genes whose expression were present in aorta and absent in other tissues queried (including IVC) were the main focus of our analysis.

Quantitative RT-PCR (qRT-PCR) analysis: 0.5 ug of pooled (6 mice) total RNA isolated from aorta, IVC, esophagus and skin (2 mice) was used to prepare cDNA. Total RNA was purified on RNeasy mini column (Qiagen) per the manufacturer's protocol. cDNA synthesis was performed using random primers and the Superscript First-Strand Synthesis System for RT-PCR (Invitrogen). SYBR green qRT-PCR was performed with 1 ul of cDNA reverse transcribed, 100 nM of gene-specific primers, and SYBR green master mix (Applied Biosystems) in an Applied Biosystems ABI Prism 7700 sequence detector according to the manufacturer's protocol. Four or five serial dilutions of cDNA were used to create a standard curve from cycle thresholds allowing comparisons between samples. A standard curve of cycle thresholds for 18S ribosomal RNA transcript was used to normalize between groups. All primer sets were analyzed with RT+cDNA, RT−cDNA and no template control prior to experimental use. The average of duplicate qRT-PCR reactions for an experiment was used to quantify the amount of mRNA relative to the standard curve. All PCR reactions were performed in triplicate. Gene-specific primers were designed using Primer Express 1.0 (Applied Biosystems) and spanned an intron for all genes studied. Amplification of a single PCR product of the expected size was confirmed by polyacrylamide gel electrophoresis and confirmed a single product using the dissociation curve. The average fold-induction and standard error for the distinct genes were calculated for each condition. Sequences for the primer sets are available upon request.

Immunofluorescence: Segments of human thoracic aorta and IVC were obtained from 3 autopsies from both male and female subjects (who did not have a vascular cause of death). Five-micron sections were prepared from formalin-fixed, paraffin-embedded tissue blocks. After deparaffinization, sections were submitted to heat-induced epitope retrieval by boiling for 11 minutes in 0.01 mol/L sodium citrate buffer (pH 6.0). Some of the human vascular tissue was embedded in OCT and flash frozen. For immunofluorescence of frozen sections, sections were fixed for 20 min at 4° C. in 100% acetone. Both formalin-fixed and frozen sections were processed similarly from this point forward. Slides were incubated with PBS-blocking buffer (0.01 g/ml BSA, 2 g powdered milk/ml, 3 □l/ml triton X-100) and 10% goat serum for 1-2 hours. The slides were then washed with PBS and incubated with primary antibody in PBS-BB/10% goat serum overnight at 4° C. The primary antibodies utilized recognized: Cytokeratin 13 (1:25, Dako), SPRR3 (1:200, Alexis Biochemicals), Isopeptide (1:400, Novus Biologicals), Plakoglobin (1:200, Sigma), Galectin-7 (1:200, a kind gift from Dr. Thierry Magnaldo), Sciellin (1:300, kind gift from Dr. Howard Baden), and Desmocollin 1 (1:50, Research Diagnostics, Inc.) Slides were washed and then incubated with appropriate secondary antibodies conjugated to fluorochromes (Molecular Probes). Slides were sealed with Vectashield mounting media (Vector Laboratories) with DAPI. SPRR3 and keratin 13 were also analyzed by immunohistochemical staining on a Ventana Gen System (Ventana Medical Systems), and immunostained sections were counterstained with hematoxylin. To ensure specificity, control slides for mouse monoclonal antibodies were incubated with irrelevant mouse antibody of the same IgG subclass whereas control slides for rabbit polyclonals were incubated with normal rabbit serum (Dako) prior to incubation with secondary antibodies. To rule out autoflourescence, the other channels were evaluated at similar exposure time. Slides were viewed on a Nikon Microphot-SA fluorescence microscope and images captured using a Colorview camera and analySIS software.

Western Analysis: Human vascular tissue was obtained through collaboration with Dr. Davis Drinkwater and Paul Chang in the Vanderbilt Department of Surgery through an IRB approved protocol from discarded material and from human heart explants. Tissues were homogenized in tissue lysis buffer (1% (w/v) Triton X-114, 10 mM Tris CL, pH 7.4, 15 mM NaCl, 1 mM EDTA, 5 ul/ml of proteinase inhibitor stock [Sigma]) and 20 ug of proteins were separated by electrophoresis through a 10% sodium dodecyl sulfate polyacrylamide gel and transferred onto nitrocellulose membranes. The blots were probed with antibodies against plakoglobin (Sigma) or SPRR3 (Alexis Biochemicals), and β-actin (Sigma) as loading control Specific antibody-antigen complexes were detected by using the ECL Western Blot Detection Kit (Amersham Pharmacia Biotech).

Results and Discussion

Gene Expression Analysis Shows Overlap Between Skin and Aorta Expressed Genes

Of the genes queried (12,000 probe sets, 8,619 Unigene Clusters), mRNAs represented by 150 probe sets were upregulated in the aorta over the IVC by >two-fold. To determine which genes specifically discriminated for the aorta, we used Affymetrix and Spotfire software to identify a set of genes that were determined to be present in the aorta but absent in murine IVC, spleen, liver, kidney, brain, skeletal muscle, lung, pancreas, intestine and heart by the call metric of the Affymetric Analysis Software. Transcripts represented by 93 probe sets were identified that were present in the aorta and absent in the IVC and in all other tissues utilized in the comparison. A subset of the probesets (50), however, were absent from the Mu74A (version 1) utilized to analyze the other tissues (with the exception of the IVC and heart) and, hence, their expression in these tissues could not be determined. To our surprise, a striking number (22/93, 24%) of the genes expressed specifically in the aorta were previously reported to be enriched in skin and other stratified epithelia (Table 1)7,8. In fact, using our analysis strategy the skin-associated signature genes represented 18 out of the 40 highest-ranking signature genes in the experiment (Table 1).

The various tissues used in our initial analysis to select for aorta enriched genes did not include stratified epithelia. Hence, to rule out the possibility that the significant overlap between the genes expressed in the aorta and skin/stratified epithelia was not merely the result of our analysis strategy, we performed microarray analysis on pooled mouse skin RNA. We additionally examined the subset of genes co-expressed in the aorta with each of the other tissues, i.e. heart, lung, spleen, etc., but which were absent in all other remaining tissues. This analysis was expected to identify a list of organ-specific (such as cardiac or liver) signature genes that were also expressed in the aorta. We were surprised to find that the liver, spleen, intestine, brain, heart and lung contained an overlap of only two or three genes with the aorta. Furthermore, none of these genes represented tissue-enriched signature genes. The pancreas and skeletal muscle contained no genes in common with the aorta by this analysis. By contrast, 15% (22/147) of the genes present in the skin but absent in IVC, spleen, liver, kidney, brain, skeletal muscle, lung, pancreas, and intestine, were also present in the aorta, confirming the unexpected prevalence discerned by our initial analysis (data not shown). Most of the genes that were co-expressed in the aorta and skin represented ones that were known to be highly enriched in other stratified epithelia and have association with important barrier/mechanical functions in these tissues9.

Common Features of CE in Skin and Aorta

We chose to further pursue this novel aorta/stratified epithelium common gene association (Table 1). They fell into two broad but overlapping categories. 1) A group of six genes, including four members of the small proline-rich protein (SPRR) family, calpactin and NICE-1 have been mapped to the epidermal differentiation complex (EDC), a region containing many genes vital to epidermal differentiation8,10. 2) A group of adhesive junction-related genes discussed below. Interestingly, many of the genes identified that fall within the first category, such as cytokerain 13, SPRRs, sceilin, and members of the S-100 calcium binding protein family, are known to be involved in the formation of the cornified cell envelope (CE)11. Terminally differentiating stratified squamous epithelial cells assemble a specialized structure on their periphery termed CE that is composed of numerous structural proteins that become cross-linked by several transglutaminase enzymes into a macromolecular assembly that is critical to the mechanical and barrier properties of this tissue9,12. Some CE precursors have been described in non-stratified epithelial that have barrier properties13,14. For example, the SPRR family members also serve as cross-bridging proteins linked to desrosomal desmoplakin and sciellin has been identified in simple epithelia with barrier properties, like the amnion, that lack a CE15,16. In general, however, expression of many of the CE precursor proteins outside of stratified epithelia, specifically vascular tissue, has not been described. The expression of several CE precursor genes in the aorta led us to further query the GeneChip data to identify the vascular expression profile of other known components of the CE (Table 2).

Cell Adhesive Junction-Related Genes are Enriched in the Aorta Over IVC

A second subset of the skin-enriched genes identified in our microarray analysis represented components of adhesive junctions involved in cell-cell adhesion (Table 1 and 2). Desmocollin I belongs to a family of desmosomal cadherins23, 24. We were especially surprised by the identification of desmocollin I in the aorta since desmosomes have not been detected in ultrastructural analysis of large vessels24. Expression of other desnosomal cadherins, desmocollin 2 and desmoglein 2, were also detected in low levels in both aorta and IVC with similar signal intensity (data not shown) whereas desmocollin 3 was undetectable in both murine aorta and IVC. Desmoplakin, an intracellular component of desmosomes and adherens junctions whose loss results in unexpected vascular abnormalities, was not queried on the chip24, 25.

Plakophilin I is a member of the armadillo family of arm proteins that directly interact with cadherens located in both adherens junctions and desmosomes (Table 1)24. These junctions play an important role in providing strength to tissues that experience mechanical stress such as heart and epidermis and their components are highly expressed in these tissues24, 26,27. Plakoglobin belongs to the same family as plakophilin I, has a similar role in adhesive junctions, and has been shown to be important in interendothelial adhesion during shear stress28. We determined if expression of plakoglobin was also enriched in the aorta. Plakoglobin expression in the murine aorta by microarray analysis was only modestly higher than in the IVC (~two-fold) (Table 2).

Quantitative RT-PCR Confirm Microarray Results

For a subset of the genes, quantitative RT-PCR (qRT-PCR) was used as an independent method to confirm the gene expression differences between the artery and IVC and to compare the relative expression in the murine aorta to other tissues containing cornified stratified epithelia such as the esophagus and skin (Table 2). For the majority of the genes tested that were called "absent" in the IVC by microarray analysis, the transcript was undetectable by qRT-PCR with a separate set of experimental samples (Table 2). However, low levels of galectin 7 expression (45-fold less than that in the aorta) were detected in the IVC by qRT-PCR. The precise function of galectin 7 is not yet known, however, it has been shown to be expressed throughout all the layers of the skin as well as the cornea and esophagus29. Its expression is linked to differentiation of skin30. The relative expression of many of these skin-enriched genes in the aorta, relative to mouse skin by qRT-PCR analysis varied (Table 2) with generally higher expression in murine skin. However, the mRNA expression of SPRR3 and TG3 was higher in aorta than skin. Interestingly, the level of expression of many of the genes involved in CE in the murine aorta was comparable to expression levels detected in the murine esophagus, a tissue with a defined CE (Table 2).

The magnitude of overexpression determined by qRT-PCR was similar to that determined from the signal intensity on the microarray for most of the genes except for plakoglobin. The relative expression of plakoglobin in the aorta was approximately 18-fold higher than in the IVC by qRT-PCR whereas the difference was only 2-fold by microarray analysis (Table 1). The aorta-specific expression of desmocollin I and plakophilin I was also verified by qRT-PCR. Desmocollin I was detected in the aorta only at a relatively low level (signal intensity of 439). This is supported by the finding that expression in the aorta was >170-fold less than in murine skin.

Protein Expression of Selected Murine Aorta-Enriched Genes in Human Aorta and Other Arteries Immunofluorescence and immunohistochemistry analysis using vascular tissue obtained from human autopsy samples was used to confirm if protein expression was restricted only to the aorta and also to determine the vascular localization of a subset of these proteins. In each analysis (except for cytokeratin 13), the same slide was also stained with the nucleic acid dye 4',6-diamidino-2-phenylindole dihydrochloride (DAPI) to determine cellular localization within the tissue.

Expression of sciellin, galectin 7, SPRR3, and cytokeratin 13 was restricted to the human aorta (data not shown). Expression of sciellin and cytokeratin 13 was restricted to the intimae of the aorta with the majority of the staining in the portion of intimae closest to the lumen (data not shown).

Comparison of Adult Aorta Gene Expression with Reported Artery/Vein Specified Genes There are only a few known artery- or vein-specific genes5, 6. EphrinB2 was the first gene to be described that is expressed in an arterial-specific manner in early embryogenesis. Later studies suggested that expression of EphrinB2 was also primarily artery-specific in adult mice32. However, analysis of the dorsal aorta and vena cava of adult mice in whole mount revealed expression in isolated endothelial cells and in the vasa vasorum of the vena cava. Although, EphrinB4 is considered specific for veins, individual EphB4-positive cells, however, were detected in the dorsal aorta. Hence, although the cellular localization of EphrinB2 and Ephrin B4 between the aorta and IVC is distinct in adult murine large vessels, there is reported expression of these proteins in both vessels. Consistent with this finding EphrinB2 message was detected in relatively similar levels in both mouse aorta and vein in our microarray analysis (Table 3). In addition to Ephrins (known to be expressed in endothelial cells and smooth muscle cells), several other smooth muscle markers such as Sox-13, EPAS-1, HRT1-3 have been reported to be arterial specific6. More recently, Lawson and colleagues have described the expression of the Notch and Gridlock family of genes in precursors of endothelial cells in which they promote arterial fate and repress venous differentiation33-35. Unlike the Ephrin genes, these and other differentially expressed genes thus far described between arteries and veins have been pronounced or even limited to differences existing only during early development35. Their expression prior to the onset of circulation suggests that at least some aspects of artery and venous differentiation are genetically determined. The expression profile of some of these genes in our microarray analysis is provided in Table 3. Consistent with published reports, these genes do not appear to have artery-enriched expression in adult mice.

Several reports have also utilized microarray analysis to identify the molecular basis for the structural and functional diversity in vessels, particularly in endothelial cells. Many of these studies have been aimed at the identification of endothelial genes that are regulated by arterial levels of shear stress. These studies have primarily focused on the analysis of transcriptional changes in a primary endothelial cell type, HUVEC, for example, under different in vitro models of shear stress36-38. Such studies have identified various genes that appear to be flow related such as lung kruppel-like factor (LKLF), superoxide dismutase (SOD), ICAM and others36-39. The message detection levels of most of these genes, with the exception of SOD, identified by in vitro shear stress models were detected both in the aorta and IVC at similar levels in our analysis (Table 3). Interestingly, VCAM has been described as down-regulated by shear stress. Our data suggests that VCAM transcript was reduced by two-fold in the aorta over IVC.

Using gene array to compare the gene expression profile of the aorta and IVC, we have identified several genes that are specifically expressed in the aorta and not the IVC. A surprising number of these aorta-specific genes are also enriched in stratified epithelia such as the epidermis8. A number of these represented precursors of the CE and proteins involved in adhesive junctions8,9. Interestingly, these proteins serve to enable stratified epithelia to retain important barrier properties and withstand biomechanical stress9. The identification of such a large number of known CE precursor proteins as well as proteins involved in cell-cell adhesion, expressed specifically or at least highly enriched in the murine aorta (a subset also confirmed in human aorta) over the IVC, suggests that they may play a role in the long-recognized enhanced barrier and stress-bearing properties of the aorta17. The entire arterial circulation is subject to similar biomechanical force. Our data showing that at least two of the proteins, plakoglobin and SPRR3, are expressed in similar levels in various arteries support our suggested role for these proteins. Although the aorta has a number of CE precursors, it lacks some of the important components such as involucrin and loricrin. It is suggested that involucrin is a ubiquitous component of CEs in all stratified epithelia12. Together with the fact that a CE has not been morphologically demonstrated in the aorta or large arteries, it is unlikely that the aorta contains a classic CE. However, this data raises the possibility that it may contain a less well-developed CE. Alternatively, these precursors may be participating in the cytoplasmic crosslinking of structural proteins. The human phenotype of known mutations in a few CE precursors usually manifests as various skin deformities such as ichthyosis and hyperkeratosis. Although, vascular defects in such conditions have not been yet appreciated and linked, it will be interesting to study such patients to determine if there is greater predisposition to arterial pathology, such as atherosclerosis or aneurysms.

By immunofluorescence analysis, we determined that a subset of these aorta-enriched proteins exhibited a primarily intimae-restricted expression as determined by analysis of segments of human thoracic aorta Expression of SPRR3, specifically, appears to be associated with atherosclerotic plaques. The biomechanical disruptions around atherosclerotic plaques has been long described but not well understood 40. Interestingly, the intimae at birth is limited to a lamina of endothelial cells closely abutting the internal elastic lamina. During growth and development there is proliferation and development of the intimae to approximately 0.2 mm in adult 1. It is hypothesized that biomechanical stress represents an important stimulus for differentiation of not just the endothelium, but the entire intimae in responding to the biomechanical stresses1,3. The vascular endothelium may be acting in concert with surrounding intimae to establish and maintain a flow-adapted arterial phenotype in vivo. It will be interesting to study the distribution of these proteins in different regions of the aorta, in the context of aortic disease, as well as in other large arteries and to study their expression during development.

TABLE 1

Identification of aorta-enriched genes by microarray analysis

| Genes | Signal in aorta | Locus Link ID | Function* |
|---|---|---|---|
| | | | Functions in cornification of stratified epithelia |
| Cytokeratin 13 | 50,380 | 16663 | Maintains cell shape and structurally coordinates cell cornified envelope assembly |
| Small proline rich (SPRR3) | 38,536 | 20766 | Identified in EDC[#]. Member of the cornified envelope precursor protein family; Believed to be cross-bridging proteins affecting biomechanical properties |
| SPRR1a | 11,771 | 20753 | |
| SPRR2J | 3117 | 20764 | |
| SPRR 1B | 1941 | 20754 | |
| Sciellin | 1544 | 64929 | Assembly of cornified epithelium envelope; possible role in cornified envelope scaffolding |
| S100 calcium binding protein (calpactin) | 783 | 20194 | Identified in EDC[#]. Binds calcium and annexins, expressed in keratinocytes and may be involved in cornified envelope initiation |
| | | | Enriched in stratified (cornified) epithelia |
| Keratinocyte differentiation associated protein (Kdap) | 41,134 | 64661 | Expressed in the suprabasal layer of embryonic skin |
| NICE-1 | 29,363 | 74175 | Identified in the EDC[#]; upregulated in differentiated keratinocytes |
| EST | 25,576 | 67855 | Isolated from skin library: function unknown |
| Calmodulin 4 | 21,644 | 80796 | Expressed in epidermis; Can associate with transglutaminase 3 and believed to be important in terminal differentiation of keratinocytes |
| Lectin, galactose binding, soluble 7 (galectin 7) | 21,157 | 16858 | Expressed in all layers of the epidermis; function unknown |
| Metallothionein IV | 20,751 | 17752 | Expressed in stratum spinosum of mouse tongue, esophagus and upper stomach |
| Arachidonate 12-lipoxygenase 12R type | 3,563 | 11686 | Expressed in skin; mutated in non-bullous congenital ichthyosiform erythroderma |
| Tyrosine hydroxylase | 1,589 | 21823 | Identified in melanocytes and cultured epithelium |
| Cellular retinoic acid binding protein II (CRABP2) | 1,523 | 12904 | Involved in retinoic acid-mediated regulation of skin growth |
| Procollagen, type XVII, alpha 1 | 1,128 | 12821 | Transmembrane; localized to where hemidesmosomes mediates adhesion of keratinocytes to underlying membrane. Mutations associated with epidermolysis bullosa. |
| Procollagen XV, alpha 1 | 650 | 12819 | Identified in adult skin and capillaries and basement membrane of muscle |
| N-sulfotransferase | 484 | 53315 | Marker of keratinocyte differentiation |
| Protein tyrosine phosphatase, type 5 | 194 | 19024 | Striatum-enriched in humans |
| | | | Functions in cell adhesion |
| Plakophilin 1 | 5,207 | 18772 | Cutaneous cell-cell adhesion and epidermal morphogenesis Member of armadillo protein family and component of desmosomes |
| Desmocollin 1 | 439 | 13505 | Calcium dependent glycoprotein of the cadherin superfamily. Constitutes the adhesive proteins of the desmosome cell-cell junction |

*Genes identified were queried against public databases (NCBI LocusLink, NCBI PubMed, Gene Ontology Consortium and OMIM to assign a functional classification.
[#]Epidermal differentiation Complex is a region on 1q21 that is comprised of a large number of genes important in maturation of the human epidermis.

TABLE 2

Transcripts of genes enriched in stratified epithelia are expressed specifically in murine aorta by genechip and qRT-PCR analysis

| Genes | Fold Δ aorta:IVC** | qRT-PCR Relative levels | | | | Fold Δ A:IVC | FoldΔ A:Eso | Fold Δ A:Skin |
|---|---|---|---|---|---|---|---|---|
| | | Aorta | IVC | Esophagus | Skin | | | |
| Cytokeratin 13 | N/A# | 129 ± 12 | UD | 19 ± 4.2 | 0.01 ± 0.02 | ND$ | 6.8 | 12900 |
| | | | Genes involved in cornification | | | | | |
| SPRR1a | N/A | 60 ± 11 | UD* | 61 ± 5.8 | 640 ± 58 | ND | 0.98 | 0.09 |
| SPRR3 | N/A | 120 ± 34 | UD | 10 ± 7.0 | 0.72 ± 0.78 | ND | 12 | 170@ |
| Sciellin | N/A | 12 ± 4.3 | UD | 23 ± 2.8 | 52 ± 12 | ND | 0.52 | 0.23 |
| Periplakin | 14 | 29 ± 4.1 | 1.0 ± 1.0 | 7.7 ± 6.4 | 550 ± 73 | 29 | 3.8 | 0.05 |
| Envoplakin | Not present on chip | 200 ± 55 | 12 ± 4.0 | 200 ± 86 | 1000 ± 79 | 17 | 1.0 | 0.02 |
| Transglutaminase I | Not present on chip | 68 ± 19 | UD | 72 ± 22 | 153 ± 29 | ND | 0.94 | 0.44 |
| Transglutaminase III | 15 | 97 ± 15 | 14 ± 2 | 260 ± 16 | 69 ± 8.6 | 7 | 0.37 | 1.4 |
| | | | Genes involved in cell—cell adhesion | | | | | |
| Desmocollin I | N/A | 140 ± 11 | UD | 0.6 ± 0.35 | 24000 ± 290 | ND | 230 | 0.005 |
| Plakophilin I | N/A | 160 ± 11 | UD | 0.52 ± 0.51 | 1900 ± 830 | ND | 310 | 0.08 |
| Plakoglobin | 2 | 160 ± 19 | 12 ± 2.2 | 1600 ± 0.73 | 5300 ± 10 | 13 | 0.1 | 0.03 |
| | | | Other genes identified by microarray analysis | | | | | |
| Nice-1 | N/A | 24 ± 8.0 | UD | 5.5 ± 1.7 | 110 ± 57 | ND | 4.4 | 0.22 |
| Galectin 7 | N/A | 120 ± 13 | 2.7 ± 0.71 | 47 ± 5.2 | 840 ± 91 | 45 | 2.6 | 0.14 |

**Denotes microarray data
N/A: Not applicable since expression in IVC not detected.
*UD: mRNA undetected by QRT-PCR
$ND-Not determined because expression limited to aorta by qRT-PCR.
@Unlike majority of the SPRR family, expression described to be low in skin, high in esophagus, cervix.

TABLE 3

Expression of previously known artery-specific or shear stress/flow-regulated genes

| Known Artery or Vein-enriched Genes | Tissue enriched | Signal in aorta | Signal in IVC | Fold Δ A: IVC |
|---|---|---|---|---|
| Ephrin B2 | artery | 1276 | 1684 | 0.76 |
| Ephrin B4 | vein | N/A* | N/A | N/A |
| Notch 3 | artery | 1577 | 2017 | 0.78 |
| Sox-13 | artery | 3424 | 2347 | 1.5 |
| Known shear-regulated genes | Regulation with shear | | | |
| Thioredoxin reductase | Upregulated | 2198 | 2279 | 0.96 |
| SGK | Upregulated | 4261 | 5107 | 0.83 |
| Id2 | Upregulated | ND# | ND | ND |
| ICAM1 | Upregulated | 417 | 536 | 0.78 |
| Smad 8 | Upregulated | N/A | N/A | N/A |
| Smad 6 | Upregulated | 1462 | 1971 | 0.74 |
| Smad 7 | Upregulated | 1412 | 1888 | 0.75 |
| GADD34 | Upregulated | N/A | N/A | N/A |
| LKLF | Upregulated | ND | ND | ND |
| EC-NOS | Upregulated | ND | ND | ND |
| SOD | Upregulated | 16446 | 11770 | 1.4 |
| COX2 | Upregulated | ND | ND | ND |
| Endothelin | Downregulated | ND | ND | ND |
| VCAM | Downregulated | 411 | 704 | 0.58 |

*Not present on chip.
Expression of gene not detected

Figure and Table Legends:

Table 2. Several genes identified by microarray analysis as well and additional genes involved in epithelial barrier function were tested by qRT-PCR to determine relative expression among murine aorta, IVC, skin and esophagus. Column 2 denotes fold change in signal intensity determined from affymetrix microarray suite analysis of the GeneChip data. Columns 3-6 shows the average of duplicate qRT-PCR reactions used to quantify the amount of mRNA relative to the standard curve. Four or five serial dilutions of cDNA were used to create a standard curve from cycle thresholds allowing comparisons between samples. A standard curve of cycle thresholds for 18S ribosomal RNA transcript was used to normalize between groups. Columns 7-9 show fold change of expression between the aorta and designated tissue of as determined by qRT-PCR.

REFERENCES

1. Stehbens W E: Structural and architectural changes during arterial development and the role of hemodynamics. Acta Anat 1996, 157:261-274

2. Mills L Sumpio B E: Vascular smooth muscle cells. Armonk, N.Y., Futura Publishing Company, Inc., 1997, pp 187-226

3. Fry D L: Arterial intimal-medial permeability and coevolving structural responses to defined shear-stress exposures. Am J Physiol Heart Circ Physiol 2002, 283:H2341-H2355

4. Schwartz S M, Majesky M W, Murry C E: The intima: development and monoclonal responses to injury. Atherosclerosis 1995, 118:S125-S140

5. Cleaver O, Melton D A: Endothelial signaling during development Nature Med 2003, 9:661-668

6. Carmeliet P: Angiogenesis in health and disease. Nature Med 2003, 9:653-660

7. Curto E V, Lambert G W, Davis R L, Wilborn T W, Dooley T P: Biomarkers of human skin cells identified using dermarray DNA arrays and new bioinformatics methods. Biochem Biophys Res Comm 2002, 291:1052-1064

8. Marenholz I, Zirra M, Fischer D F, Backendorf C, Ziegler A, Mischke D: Identification of human epidermal differentiation complex (EDC)-encoded genes by subtractive hybridization of entire YACs to a gridded keratinocyte cDNA library. Genome Res 2001, 11:341-355

9. Kalinin A E, Kajava A V, Steinert P M: Epithelial barrier function: assembly and structural features of the cornified cell envelope. BioEssays 2002, 24:789-800

10. Gibbs S, Funeman R, Wiegant J, Gerts van Kessel A, Putte P, Backendorf C: Molecular characterization and evolution of the SPRR family of keratinocyte differentiation markers encoding small proline-rich proteins. Genomics 1993, 16:630-637

11. Jarnik M, Kartasova T, Steinert P M, Lichti U, Steven A C: Differential expression and cell envelope incorporation of small proline-rich protein 1 in different cornified epithelia J Cell Science 1996, 109:1381-1391

12. Nemes Z, Steinert P M: Bricks and mortar of the epidermal barrier. Exp Mol Med 1999, 31:5-19

13. Bonilla I E, Tanabe K, Strittmatter S M: Small proline-rich repeat protein 1A is expressed by axotomized neurons and promotes axonal outgrowth. J Neuroscience 2002, 22:1303-1315

14. Cabral A, Voskamp P, Cleton-Jansen A, South A, Nizetic D, Backendorf C: Structural organization and regulation of the small proline-rich family of cornified envelope precursors suggest a role in adaptive barrier function. J Biol Chem 2001, 26:19231-19237

15. Champliaud M, Baden H P, Koch M, Jin W, Burgeson R E, Viel A: Gene characterization of sciellin (SCEL) and protein localization in vertebrate epithelia displaying barrier properties. Genomics 2000, 70:264-268

16. Baden H P, Kvedar J C: Epithelial cornified envelope precursors are in the hair follicle. J Invest Dermatol 1993, 101:72S-74S 17. Kwei S, Stavrakis G, Takahas M, Taylor G, Folkman M J, Gimbrone M A, Garcia-Cardena G: Early adaptive responses of the vascular wall during venous arterialization in mice. Am J Pathol 2004, 164:81-89

18. Karashima T, Watt F M: Interaction of periplakin and envoplakin with intermediate filaments. J Cell Science 2002, 115:5027-5037

19. Fuchs E, Weber K: Intermediate filaments: structure, dynamics, function, and disease. Annu Rev Biochem 1994, 63:345-382

20. Waseem A, Alam Y, Dogan B, White K N, Leigh I M, Waseem N H: Isolation, sequence and expression of the gene encoding human keratin 13. Gene 1998, 215:269-279

21. Johansson B, Eriksson A, Thornell L: Intermediate filament proteins in developing human arteries. Anat Embryol 1998, 199:225-231

22. Marshall D, Hardman M J, Nield K M, Byrne C: Differentially expressed late constituents of the epidermal cornified envelope. Proc Natl Acad Sci, USA 2001, 98:13031-13036

23. North A J, Bardsley W G, Hyam J, Bornslaeger E A, Cordingley H C, Trinnaman B, Hatzfeld M, Green K J, Magee A I, Garrod D R: Molecular map of the desmosomal plaque. J Cell Science 1999, 112:4325-4336

24. Vestweber D: Molecular mechanisms that control endothelial cell contacts. J Pathol 2000, 190:281-291

25. Gallicano G I, Bauer C, Fuchs E: Rescuing desmoplakin function in extra-embryonic ectoderm reveals the importance of this protein in embryonic heart, neuroepithelium, skin and vasculature. Development 2001, 128:929-941

26. Schnittler H J, Puschel B, Drenchkhahn D: Role of cadherins and plakoglobin in interendothelial adhesion under resting conditions and shear stress. Am J Physiol Heart Circ Physiol 1997, 273:H23296-H22405

27. Troyanovsky R B, Chitaev N A, Troyanovsky S M: Cadherin binding sites of plakoglobin: localization, specificity and role in targeting to adhering junctions. J Cell Science 1996, 109:3069-3078

28. Hoffmann I, Mertens C, Brettel M, Nimmrich V, Schnolzer M, Herrmann H: Interaction of plakophilins with desmoplakin and intermediate filament proteins: an in vitro analysis. J Cell Science 2000, 113:2471-2483

29. Magnaldo T, Darmon M: Galectin-7, a new marker of mammalian stratified epithelia Trends Glycoscience Glycotechnology 1997, 9:95-102

30. Timmons P M, Colnot C, Cail I, Poirier F, Magnaldo T: Expression of galectin-7 during epithelial development coincides with the onset of stratification. Int J Dev Biol 1999, 43:229-235

31. Haroon Z, Wannenburg T, Gupta M, Greenberg C S, Wallin R, Sane D C: Localization of tissue transglutaminase in human carotid and coronary artery atherosclerosis: implications for plaque stability and progression. Lab Invest 2001, 81:83-93

32. Gale N W, Baluk P, Pan L, Kwan M, Holash J, DeChiara T M, McDonald D M, Yancopoulos G D: Ephrin-B2 selectively marks arterial vessels and neovascularization sites in the adult, with expression in both endothelial and smooth muscle cells. Develop Biol 2001, 230:151-160

33. Lawson N D, Vogel A M, Weinstein B M: Sonic hedgehog and vascular endothelial growth factor acts upstream of the notch pathway during arterial endothelial differentiation. Develop Cell 2002, 3:127-136

34. Zhong T P, Childs S, Leu J P, Fishman M C: Gridlock signalling pathway fashions the first embryonic artery. Nature 2001, 414:216-220

35. Lawson N D, Weinstein B M: Arteries and veins: making a difference with zebrafish. Nature Rev 2002, 3:674-682

36. Garcia-Cardena G, Comander J, Anderson D J, Blackman B R, Gimbrone M A: Biomechanical activation of vascular endothelium as a determinant of its functional phenotype. Proc Natl Acad Sci, USA 2001, 98:4478-4485

37. Dekker R J, van Soest S, Fontijn R D, Salamanca S, de Groot P G, VanBavel E, Pannekoek H, Horrevoets A J: Prolonged fluid shear stress induces a distinct set of endothelial cell genes, most specifically lung Kruppel-like factor (KLF2). Blood 2002, 100:1689-1698

38. Chen B P, Li Y, Zhao Y, Chen K, Li S, Lao J, Yuan S, Shyy J Y, Chien S: DNA microarray analysis of gene expression in endothelial cells in response to 24-h shear stress. Physiol Genomics 2001, 7:55-63

39. Wasserman S M, HMehraban F, Komuves L G, Yang R, Tomlinson J E, Zhang Y, Spriggs F, Topper J N; Gene expression profile of human endothelial cells exposed to sustained fluid shear stress. Physiol Genomics 2002, 12:13-23

40. Salunke N V, Topoleski L D T, Humphrey J D, Mergner W J: Compressive stress-relaxation of human atherosclerotic plaque. J Biomed Mater Res 2001, 55:236-241.

In summary, the inventors discovered that a SPRR3 gene product which is expressed in intimae in a living human is a biomarker for diagnosis of increased risk and progression of atherosclerosis. This biomarker is a therapeutic tool for achieving successful preventative intervention. The presence of this biomarker is clear evidence of the unfortunate progression from normal intimae tissue to atherosclerosis. This biomarker also provides a clinical method for identifying a preventative agent that could possibly reverse or retard the undesired and unfortunate vascular molecular events leading to the expression of SPRR3. The detection of SPRR3 is useful to predict atherosclerotic changes in the vessels wall and as such is a predictor of stroke, peripheral arterial disease, atherothrombosis and myocardial infarction.

While the discovery has been described in terms of various specific embodiments, those skilled in the art will recognize that the invention can be practiced with modification within the spirit and scope of the claims.

---

What is claimed is:

1. A method for aiding in the determination of whether a living human is afflicted with atherosclerosis, the method comprising:
    determining the level of small proline-rich protein 3 (SPRR3)protein in a representative biological sample obtained from said living human, said biological sample being selected from the group consisting of an arterial biopsy sample and an arterialized vein;
    comparing the determined level of SPRR3 protein in the representative biological sample obtained from said living human with a range of SPRR3 levels previously defined as characteristic for humans having atherosclerosis; and
    concluding from said comparison that the living human is likely suffering from atherosclerosis when a SPRR3 level is in the range of SPRR3 levels previously defined as characteristic for the presence of atherosclerosis as an indication that the living human is suffering from atherosclerosis.

2. A method in accordance with claim 1 wherein said level of SPPR3 is determined by using molecular localization.

3. A method in accordance with claim 2 further comprising contacting said sample with suitably labeled antibody which recognizes SPRR3.

4. A method in accordance with claim 3 further comprising comparing the determined level of SPRR3 with a constellation of other risks characteristic for the presence of atherosclerosis as an indication that the living human is suffering from atherosclerosis.

5. A method of practicing medicine which comprises:
    determining a level of SPRR3 protein by using molecular localization on a biological sample selected from the group consisting of an arterial biopsy sample and an arterialized vein;
    comparing the determined level of SPRR3 protein in the biological sample obtained from said living human with a range of SPRR3 levels previously defined as characteristic for humans having atherosclerosis ; and
    concluding from said comparison that the living human is likely suffering from atherosclerosis when a SPRR3 level is in the range of SPRR3 levels previously defined as characteristic for the presence of atherosclerosis as an indication that the living human is suffering from atherosclerosis.

6. A method in accordance with claim 5 wherein said molecular localization comprises contacting said sample with an antibody recognizing SPRR3.

7. A method in accordance with claim 2 further comprising contacting said sample with a suitably labeled antibody which recognizes an SPRR3 gene product.

8. A method in accordance with claim 3 further comprising comparing the determined level of SPRR3 protein in the representative biological sample with a constellation of other risks characteristic for the presence of atherosclerosis as an indication that an individual is suffering from atherosclerosis.

\* \* \* \* \*